United States Patent [19]
Reitan

[11] Patent Number: 5,600,574
[45] Date of Patent: Feb. 4, 1997

[54] AUTOMATED IMAGE QUALITY CONTROL

[75] Inventor: Ronald C. Reitan, Stillwater, Minn.

[73] Assignee: Minnesota Mining and Manufacturing Company, St. Paul, Minn.

[21] Appl. No.: 242,275

[22] Filed: May 13, 1994

[51] Int. Cl.$^6$ .................................................. G06F 11/00
[52] U.S. Cl. ........................... 364/552; 364/550; 364/525
[58] Field of Search ..................................... 364/552, 550, 364/413.13, 413.14, 413.19, 525; 382/100, 128, 131, 132, 141, 149, 190, 224; 358/406, 405, 462, 504

[56] References Cited

U.S. PATENT DOCUMENTS

| | | | |
|---|---|---|---|
| H999 | 12/1991 | Merke | 364/552 |
| 4,939,581 | 7/1990 | Shalit | 358/350 |
| 5,077,768 | 12/1991 | Shigyo | 378/98 |
| 5,115,229 | 5/1992 | Shalit | 345/1 |
| 5,153,926 | 10/1992 | Jansson | 382/128 |
| 5,172,419 | 12/1992 | Manian | 382/132 |
| 5,194,966 | 3/1993 | Quardt et al. | 358/406 |
| 5,220,617 | 6/1993 | Bird et al. | 382/149 |
| 5,319,550 | 6/1994 | Griffith | 364/413.19 |
| 5,331,550 | 7/1994 | Stafford et al. | 364/413.13 |
| 5,361,307 | 11/1994 | Hartley et al. | 382/141 |
| 5,436,979 | 7/1995 | Gray et al. | 382/141 |
| 5,440,648 | 8/1995 | Roberts et al. | 382/141 |
| 5,444,480 | 8/1995 | Sumita | 382/141 |

FOREIGN PATENT DOCUMENTS

| | | |
|---|---|---|
| 518525A2 | 12/1992 | European Pat. Off. . |
| 542012A1 | 5/1993 | European Pat. Off. . |

OTHER PUBLICATIONS

Medical Imaaging 1993: Image Capture, Formatting, and Display, vol. 1897, dated Feb., 1993, (25 pages).
Article entitled: Quality Monitoring of Soft–Copy Displays for Medical Radiography, Journal of Digital Imaging, vol. 5, No. 3, (Aug.), 1992; pp. 161–167.
Article entitled: Objective Analysis of Ultrasound Images by use of a Computational Observer, IEEE Transactions on Medical Imaging, vol. 11, No. 4, Dec. 1992. (Lopez et al.).

*Primary Examiner*—James P. Trammell
*Assistant Examiner*—Hal D. Wachsman
*Attorney, Agent, or Firm*—Schwegman, Lundberg, Woessner & Kluth, P.A.

[57] ABSTRACT

A system, apparatus and method for testing the functional components of an electronic digital imaging system is described. The system includes apparatus for image acquisition, storage, display, communication and printing. The system relies on a closed loop analysis to test system components by measuring a set of statistical image quality metrics. The expected set of statistics are in the form of special purpose features stored as a data set representative of an expected reference object. The closed loop analysis measures, for example, the quality of the printing component of the system by outputting a copy of the expected reference image, using the acquisition component to input the copy of the expected reference image, and then comparing the statistics against threshold values representative of an ideally operating component. The comparison of statistics against the threshold values provides a go/no-go measure of component performance and can indicate sources of system degradation.

19 Claims, 31 Drawing Sheets

AUTOMATED IMAGE QUALITY CONTROL

FIELD OF THE INVENTION

The present invention relates to quality assurance and control of acquired and stored imagery and in particular the present invention relates to a method and apparatus for automatically insuring image quality in a medical imaging system.

BACKGROUND OF THE INVENTION

Electronic digital imaging systems are known in the art in which images are digitized and stored as digital pixel elements in a computer based system. The images can then be retrieved and displayed on display mechanisms for later use. An example of this type system is the medical field where x-ray images, computed tomography (CT) scan images, magnetic resonance imaging (MRI) data, ultrasound data and the like may be digitized and the images can be stored and retrieved from a mass storage device. By connecting a graphics monitor or a plurality of monitors to the system, a medical practitioner can retrieve the images on such a monitor on demand.

Various types of quality control have been applied to electronic digital imaging systems. For example, in U.S. Pat. No. 4,939,581 to Shalit, an attempt is made to measure the quality of gray-scale of a video monitor screen by placing a gray-scale test pattern on the CRT screen and measuring features of the test pattern using a photometer. The gray-scale test pattern is then photographed using an electronic camera, a hard copy film is produced from the electronic camera image and a densitometer reading is taken of the hard copy. The results of the densitometer readings are then used to adjust the electronic camera image for ideal luminance to compensate on a pixel-by-pixel basis to produce a gray-scale which matches the developed film.

The system of the Shalit patent only addresses control of a single image quality aspect: the gray-scale accuracy of hard copies as representations of the CRT image. In addition, the system does not treat the case of matching a CRT display to film and does not address the problem of the original CRT image quality. Since the Shalit system is only designed to match a hard copy to a CRT device, an objective display of image quality is ruled out. In order to reproduce accurate images, an objective standard needs to be applied to CRT matching and to locate sources of degradation throughout all points within an electronic imaging system, not just through the CRT display device. Without any form of system-wide degradation analysis, components of the Shalit system may affect the overall image quality of the video monitor causing the x-ray to match the video monitor for a wholly inaccurate display.

In U.S. Pat. No. 5,115,229 to Shalit, a method and system in video image reproduction is described using a gray-scale test pattern on CRT screens to compare two or more video screens. The objective of this system is to achieve a CRT-to-CRT match without regard to an objective set of criteria for CRT alignment. One of the drawbacks of the Shalit system is that k will match a good CRT with a bad CRT display such that both CRT displays will produce imagery only up to the capabilities of the poorest of the two screens. There is no ability to match the CRTs to any objective criteria to not only align the CRTs to produce the best image quality possible from that particular CRT but also to locate CRTs operating below a minimum acceptable threshold. In addition, the Shalit system merely deals with a single image quality aspect: the gray-scale accuracy between CRTs. There is a need in the art therefore to control the image quality in many categories simultaneously such as pixel value, geometric and spacial resolution characteristics.

In the paper entitled "Quality Monitoring of Soft-Copy Displays for Medical Radiography" by Reiker et al., published in the Journal of Digital Imaging, August 1992, luminance measurements from a plurality of CRT screens within a hospital or imaging center are used to compile a database of luminance information. A low cost photometer instrument with an RS-232 interface allows the device to be connected to CRT screens throughout a hospital to measure the luminance values on every display station. A software method and procedure for displaying test images of single valued luminance information allows a software program to generate luminance response curves for every display device within the organization. This provides a system for quality control of the CRT displays. The author has described this system as being necessary to calibrate the CRTs to conform with a standard luminance curve by adjusting brightness and contrast controls of the CRT stations. The shortcomings of this system, however, are that the lack of image quality control throughout the entire electronic imaging system may result in erroneous adjustments being made to CRTs at the various locations throughout the network.

There is a need in the art to control the quality of the image within an electronic digital imaging environment which is unsatisfied by existing systems. Present electronic digital imaging systems lack the ability to test, maintain and ensure the integrity of the quality of the image throughout all stages of the system including the stages of acquisition, transmission, display and hard copy generation. There is also a need in the art to measure and report system performance to a system operator in a user-friendly manner such as a simple go/no-go indicator of acceptable system performance. Further, there is a need in the art for remote diagnostic testing, predictive and preventative servicing and computer assisted fault isolation of image degradation and system failures. There is also a need in the art to provide system performance testing by using the components of the system to test themselves without the need for a field service person to carry expensive test and calibration equipment to the site. The present invention solves these and other problems which will be recognized by those skilled in the art upon reading and understanding the following specification.

SUMMARY OF THE INVENTION

The present invention is a system, apparatus and method for automatically testing the functional components of an electronic digital imaging system. The system includes apparatus for image acquisition, storage, display, communication and printing. The present invention relies on a closed-loop computer analysis to test system components by automatically measuring a set of image quality metrics derived from an analysis of a known set of features contained in special reference images. The metrics are compared to values obtained from a priori information about the expected performance of the system component under test. The closed loop analysis measures, for example, the quality of the printing component of the system by using the acquisition component to measure the output of a printing component where the input is a reference image and then testing the statistical metrics obtained from an acquired sample image to locate sources of system degradation.

The image quality metrics are known as a metrics set which contains a comprehensive set of tests regarding primary modes of image quality degradation: pixel value integrity, pixel location integrity (geometric distortion) and spatial resolution. The metrics set allows for the automatic execution of a large number of image quality measurements and a reduction of the resulting test data to a manageable result so that a simple go/no go result may be given to the system operator. In addition, the metrics set is useable in indicating and locating system faults based upon the analysis data for field service personnel.

BRIEF DESCRIPTION OF THE DRAWINGS

In the drawings, where like numerals describe like components throughout the several views.

DETAILED DESCRIPTION OF THE PREFERRED EMBODIMENT

In the following detailed description of preferred embodiment, reference is made to accompanying drawings which form a part hereof, and in which is shown, by way of illustration, specific preferred embodiments in which the invention may be practiced. These embodiments are described in sufficient detail to enable those skilled in the art to practice the invention and it is to be understood that other embodiments may be utilized and that structural, logical and electrical changes may be made without departing from spirit and the scope of the present invention. The following detailed description is, therefore, not to be taken in a limiting sense, and the scope of the present invention is defined only by the appended claims.

System Overview

Figure 1:
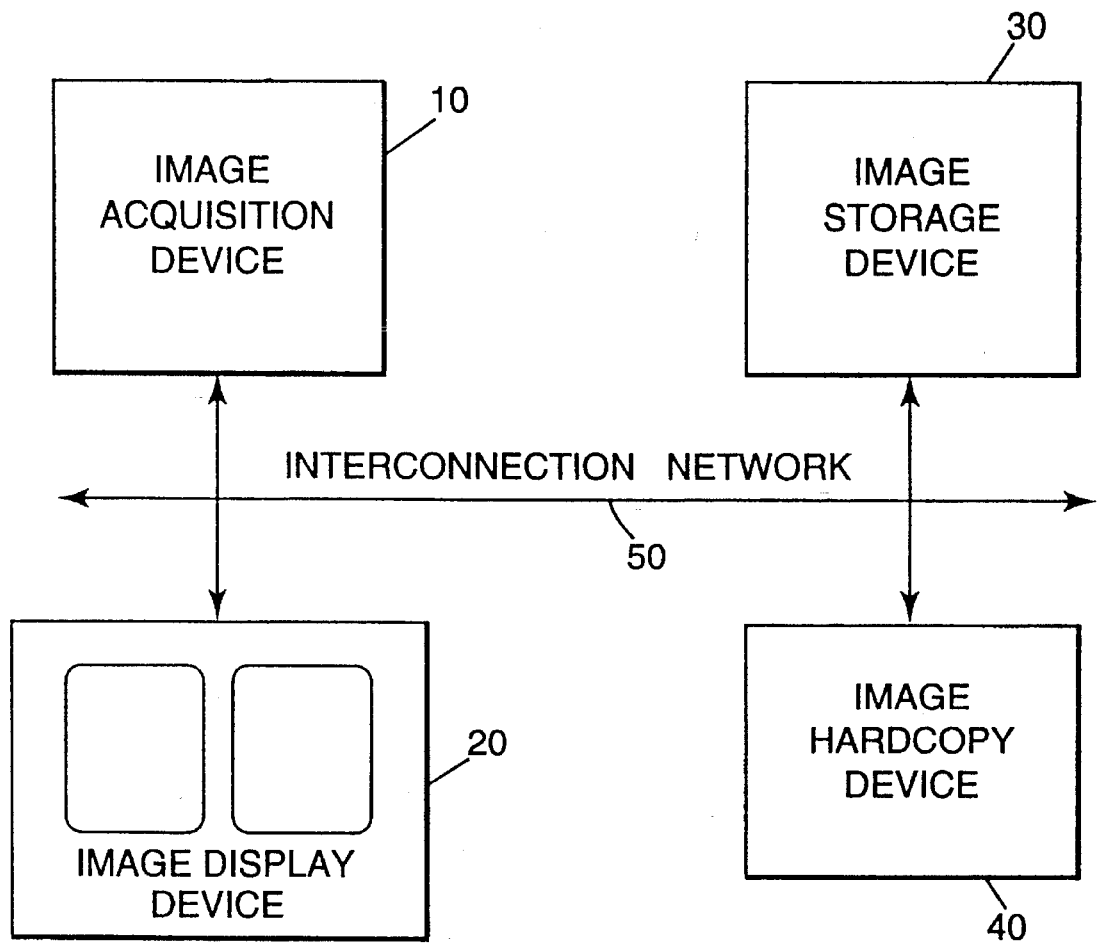
FIG. 1 is a block diagram of the components of a generalized electronic imaging system.

FIG. 1 describes a basic electronic digital imaging system. This system consists of a number of basic components which fall into general categories. The image acquisition device 10 shown in FIG. 1 includes such devices as film digitizers, scanners and other selected modalities. The image acquisition devices 10 may be a number of medical scanning modalities such as ultrasound, MRI, CT, digital radiography, and digitized conventional x-ray film. The image display device 20 may be some type of CRT device such as a high resolution computer color or monochrome monitor. The image storage device 30 is typically a mass storage device such as disk storage. The image hard copy device 40 of FIG. 1 would typically be a laser printer for paper copies of the images, a pen plotter, a printing plate output, or laser imaged onto film.

The components of the generalized electronic imaging system of FIG. 1 may be used in a variety of industries in which image acquisition, storage and retrieval is required. For example, in the publishing industry, the acquisition device 10 may be a document scanner. The hard copy device 40 in the publishing industry could be laser printers or perhaps even the output going to printing plates for offset printers or the like. The display device 20 used in the publishing industry may be used in the layup and production process.

The preferred embodiment of the present invention includes software methods for controlling the image quality within the electronic imaging environment shown on FIG. 1. The present invention utilizes a set of objective image quality metrics computed automatically from a number of sampled images. This quality control system provides consistent and thorough measurement of the quality of the image throughout the electronic imaging system, including the stages of acquisition, transmission, display, and hard copy generation. Further, the preferred embodiment of the present invention describes methods of remote diagnostic checking, predictive/preventative servicing and computer assisted fault isolation.

For purposes of example, but not by limitation, the preferred embodiment of the present invention is described in conjunction with a medical imaging and picture archiving system where each of the four blocks of FIG. 1 is typically part of a large network in which a plurality of each of the four components is duplicated and interconnected by an interconnection network 50. In other words, there are a plurality of image acquisition devices 10 and the images may be stored at a plurality of image storage device sites 30. A number of image display devices may be utilized in such places as intensive care units (ICU), cardiac care units (CCU), emergency rooms (ER), in laboratories or doctors' offices. The images are typically stored at a central location in an image storage device 30 and can be printed through the use of image hard copy devices 40 at a number of sites in a hospital or clinic to make duplicate x-rays, laser prints, film, etc. Those skilled in the art will readily recognize that the present invention is not limited to medical imaging systems but is in fact applicable to all types of electronic imaging systems.

Figure 2:
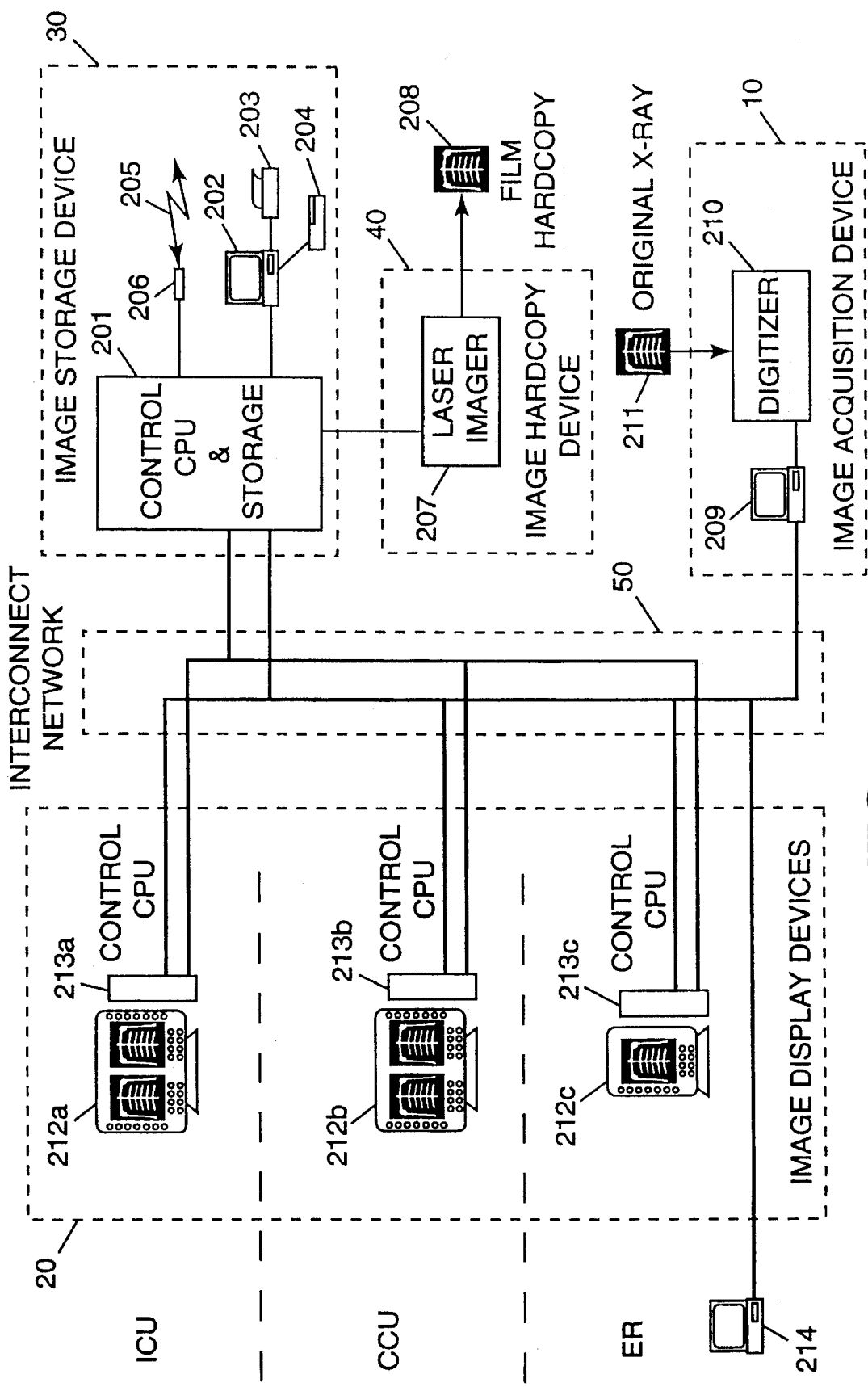
FIG. 2 is a block diagram of a particular implementation of an electronic imaging system used in a medical environment.

FIG. 2 is a block diagram describing the preferred embodiment of the present invention used in a medical environment. The system of FIG. 2 is an electronic digital imaging system known to the inventors in this case as a PACS (Picture Archiving and Communications) System manufactured by Minnesota Mining and Manufacturing Company of St. Paul, Minn. This example shows an electronic imaging system in which an ICU, CCU and ER areas are equipped with image review stations for displaying medical imagery. The image review stations are connected by an interconnection network to image storage devices, image hard copy devices and image acquisition devices.

The interconnection network 50 may be one of any number of varieties of local or wide area networks using technologies such as ethernet, FDDI, ATM, token ring etc. As shown in FIG. 2, an image server system with local administration of the network is a part of the image storage device 30 of FIG. 1. This would comprise a local control CPU and a large disk storage subsystem 201 for storing the imagery and data associated with the images which may be in the form of a network file server. A local monitor 202 may be equipped with a local printer 203 and a local disk subsystem 204. The control CPU 201 of the image storage device 30 may also be connected by remote connection 205 through modem 206 to other locations to obtain and transfer additional imagery and data associated thereto.

By way of illustration, but not by way of limitation, the image hard copy device 40 may be a laser imager 207 connected locally to the control CPU 201 of the image storage device 30. The laser imager 207 may also be connected through interconnection network 50 as a remote node on the network. A variety of outputs may be obtainable from the image hard copy device 40, but in the preferred embodiment of the present invention, a film hard copy 208 is obtained to reproduce medical imagery.

Image acquisition device 10 may also be connected as a node on the network through a control CPU 209. Digitizer 210 accepts, for example, original x-ray films 211 for input into the system. The original x-ray film 211 is digitized by digitizer 210 and stored locally in control CPU 209. The acquired image is then transferred via interconnection network 50 to the image storage device 30 where it is stored on the disk subsystem 204 under control of the control CPU 201.

All image data stored on disk subsystem 204 is available via interconnection network 50 at the various image display devices 20. As exemplified in FIG. 2, these locations may be an ICU, a CCU, or an ER. Each of these locations has an individual image review station 212a–c connected to interconnection network 50 via local control CPUs 213a–c. The image review stations may consist of single screen or double screen display devices. The double screen display device may be a double-width CRT for displaying two images side-by-side or it may consist of two physical CRTs placed side-by-side for the comparison of images.

Also available on the interconnection network 50 is a patient census information station 214 consisting of a local computer attached to interconnection network 50.

Typical Operation of Image Acquisition, Storage and Display

By way of example, the electronic imaging system of FIG. 2 in a hospital environment may be used in the ICU to care for a patient. Typically, a portable x-ray is taken of the patient in the ICU and it must be processed to determine such things as correct tube or electrode placement, the presence of pneumothorax, etc. The electronic imaging system aids the workflow by making the imagery readily available in an electronic form in the ICU and preventing film loss that might otherwise occur if the films were returned to the ICU after processing in a radiology department.

In operation, the x-ray image is first taken and the film cassette will be sent to film processing in a radiology department. The radiology department may be quite a distance removed from the ICU. The exposed film cassette is processed and immediately transferred onto the imaging system through digitizer 210 where it is stored in a central image storage device 30 for viewing by the image review station 212a in the ICU. The key to efficient operation of this system is how quickly that this turnaround can occur.

Another feature of the present system is the efficient high bandwidth capacity of interconnect network 50. Since medical images of high resolution can typically occupy between 4 and 20 megabytes, the transfer rate on network 50 must have the capacity to deliver multiple images to multiple sites in a near-simultaneous fashion. A goal for imaging medical imaging systems of the type shown in FIG. 2 is to deliver an image in about two second's time period after it has been requested.

Automated Image Quality Control Overview

The automated image quality control system for the electronic imaging system of the preferred embodiment of the present invention automatically determines the performance of the functional components of the electronic imaging system by compiling a set of statistical metrics (measurements). The statistics are computed using the pixel values and coordinates of image pixels acquired from reference objects having a number of specialized features. The performance test consists of a comparison of each metric to one or more thresholds. These thresholds are determined by prior examination or derivation of the metrics computed from a known good component of the same type. If the metrics show that the performance of a specific functional component is below an acceptable minimum threshold, or outside an acceptable range of values, a simple failure result is reported to a system operator. The specific details of how this is accomplished is best shown by actual examples.

The choice of metrics is based upon an identification of all likely modes of image quality degradation (described more fully below) using defined features which will display statistically significant changes in either its pixel values or coordinates when such degradations occur. The process of locating and extracting feature pixels required for a given metric is performed using established image processing techniques. The image processing is performed using a combination of off-the-shelf image processing library functions and custom software for computation of the special statistics.

Sources of Image Degradation

The preferred embodiment of the present invention is concerned about a number of possible deterministic aberrations which may be introduced into the viewed, stored or printed digital images as they are processed by the electronic imaging system of FIG. 2. These aberrations may be due to electronic, electro-mechanical or optical faults in any of the functional system components. These faults generally manifest themselves as a degradation in one or more of three image quality categories: pixel value integrity, geometric accuracy and spatial resolution.

By way of example, during the image acquisition process at the image acquisition device 10, the most common source of problems is contaminants within the optical path. Since most film digitizers use either scanned laser or a line-scan CCD as a means for densitometry, contamination within the optics will leads to a density error at one more fixed positions producing "streaks" in the cross scan direction. The same "streaking" problem arises with the hardcopy device printing device 40 although the source of the streaking can also include contamination within the film processor.

Other forms of pixel value distortion include electronics calibration drift, aging of the image sensor (such as the photomultiplier tube in the film digitizer 210), random errors in any serial communication and networking paths and "stuck-at" bit faults in bit-parallel data paths. The latter can occur in any of the images memories or host buses such as SCSI or other custom bit parallel data paths. Random bit errors may occur in high speed bit-serial links such as ethernet or fiber. Generally, random bit errors leading to image quality degradation are not detectable with the preferred embodiment of the present invention since a reference-based technique is used. However, if the statistical probability of these errors is high enough to ensure that the random bit errors occur during any image manipulation step, then the random errors can be treated as a pseudo-deterministic source and are detected using the present metrics approach.

Sources of geometric distortion in the imagery are usually electromechanical. These include scanning and film transport mechanisms which have nonlinear velocity characteristics due to binding, wear, belt slippage, roller contamination and deformation, etc. Also, CRT displays are especially prone to scan non-linearly as a result of electronic aging and component failure. The preferred embodiment of the present invention is not equipped to detect the geometric distortions in the display devices, as described more fully below.

Loss of spatial resolution in the image is perhaps the most subtle and potentially harmful form of degradation. In a hospital environment, medically important features may be obscured giving rise to the possibility of misdiagnosis. Loss of spatial resolution can result from all of the faults described above. The difficulty in detecting loss of spatial resolution is because the degradation is not striking in its appearance in a given image. The present invention provides specialized tests which are very sensitive to resolution loss to prevent the loss from going undetected during normal daily use of the system.

Table 1 summarizes the metrics identified as necessary to assure complete detection of known sources of degradation in an electronic image processing system. Also listed are the features (described more fully below) used to detect the sources of degradation and the statistics used to quantify the quality of the particular feature in the image.

TABLE 1

Summary of Metrics, Features and Statistical Quantifiers

| Metric Title | Applicable Components | Feature Inspected | Statistical Measures |
|---|---|---|---|
| Absolute pixel value accuracy | FD, CR, LI | Gray scale step wedge | Mean, standard deviation of absolute error |
| Acquisition/ Display response linearity | FD, CR, LI, CRT | Gray scale step wedge | Linear best fit error |
| Contrast Resolution | FD, CR, LI, CRT | Gray scale step wedge | Ratio of standard deviation to mean |
| In-scan MTF | FD, CR, LI | Vertical bar patterns | Histogram. min./max. |
| Cross-scan MTF | FD, CR, LI | Horizontal bar patterns | Histogram min./max. |
| Angular MTF | FD, CR, LI | Diagonal bar patterns | Histogram min./max. |
| In-scan velocity uniformity | FD, CR, LI | Horizontal bar | Run-length mean, standard deviation |
| Cross-scan positional jitter | FD, CR, LI | Vertical bar pattern | Run-length mean, standard deviation |
| Laser beam wobble | FD, CR, LI | Straight horizontal edge | Linear best fit error |
| Start-of-scan uniformity | FD, CR, LI | Straight vertical edge | Linear best fit error |
| End-of-scan uniformity | FD, CR, LI | Straight vertical edge | Linear best fir error |
| Absolute pixel size | FD, CR, LI | Vertical and horizontal bar patterns | Run-length absolute error |
| Pixel aspect ratio | FD, CR, LI | Vertical and horizontal bar patterns | Run-length relative error |
| Large area uniformity | FD, CR, LI | Gray scale step wedge | Maximum standard and peak deviation |
| Periphery uniformity | FD, CR, LI | Constant density border region | Peak deviation from mean deviation |
| Glare Effects | FD, CR, LI | High contrast solid box | Normalized glare area from density histogram |

TABLE 1-continued

Summary of Metrics, Features and Statistical Quantifiers

| Metric Title | Applicable Components | Feature Inspected | Statistical Measures |
| --- | --- | --- | --- |
| Streak detection | FD, CR, LI | Grey scale step wedge | Streak count, width, y-extent, polarity |
| Discrete anomalies | FD, CR, LI | Grey scale step wedge | Total discrete anomaly count |

Legend:
FD = Film Digitizer
CR = Computed Radiography
LI = Laser Imager (Hardcopy)
CRT = CRT Display

Process Flow for Image Quality Metric Computation

Figure 3:
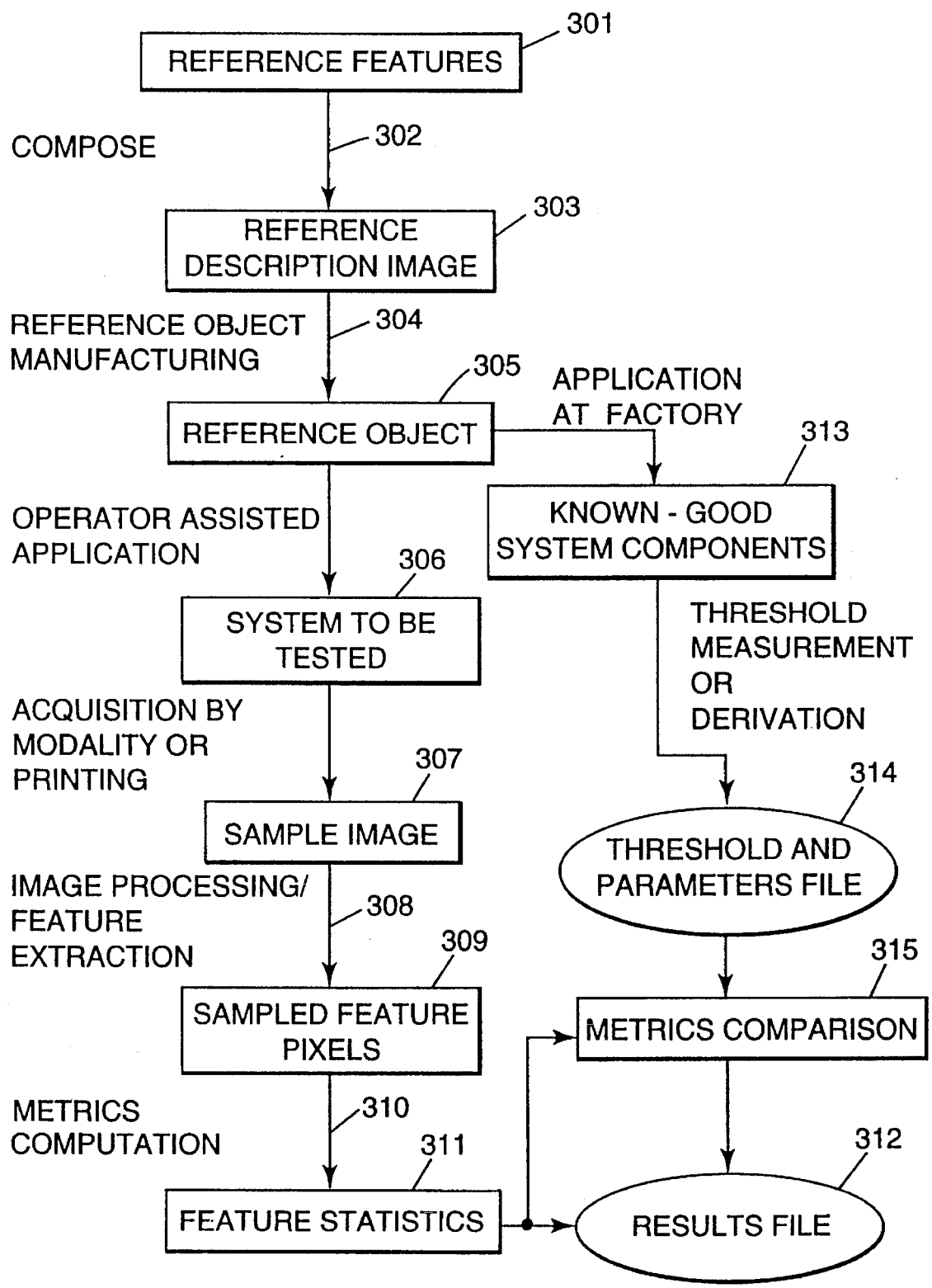
FIG. 3 is a process flow diagram for image quality metrics computation for the present invention applied to an electronic imaging system.

FIG. 3 is a process flow diagram for the image quality metrics computation of the preferred embodiment of the present invention. Reference features are first defined at 301 which are selected to locate and compute the statistical measures shown in Table 1. The reference features correspond to the features inspected in Table 1. A reference image 303 is constructed using a variety of techniques 302 described more fully below, such as printed circuit board artwork generation tools and Gerber Scientific plotters. The reference image or images 303 are then used to generate phantoms or targets as a reference object 305 using selected manufacturing techniques such as film manufacturing techniques 304 if the reference object is a film. The reference object 305 is then applied to the system to be tested at 306. The acquisition of the reference object may be through CT, MRI or ultrasound for 3D modalities or by scanning into the electronic imaging system using scanning or digitizing techniques for film. The input modality thus produces a sample image 307 from the reference object 305. Image processing 308 is then performed on the sample images 307 to locate and extract features within known regions of interest. The results is a collection of sampled feature pixels 309 representing selected features which will be used to measure system performance. Metrics computation 310 is performed on these selected features to produce a set of features statistics 311 indicating system performance. The results of these computations are then stored in a results file 312.

The reference object 305 is also used to generate data regarding expected performance of the system if all components of the system are operating at their normal or peak performance. This data set of known good system components 313 is usually generated at the factory where the systems is first assembled. From the performance of the system for the data set of known good system components 313, threshold and measurement is performed on the data and a threshold and parameters file is generated based up minimum performance values selected for acceptable system operation. Any system performance which falls below these values is considered a system failure. A metrics comparison 315 is performed at the site each time the automated image quality control system is executed to compare the thresholds and parameters file to the feature statistics file to indicate overall system performance and to indicate any failures. The results of the metrics comparison is also stored in the results file 312.

A simple go/no-go result is presented to a system operator for each component based upon a comparison of the individual statistical results to predetermined good or adequate performance limits. The results file 312 may also be used by a field technician to locate and identify components of the system which need servicing.

Automated Image Quality Control Process Flow

Figure 4A:
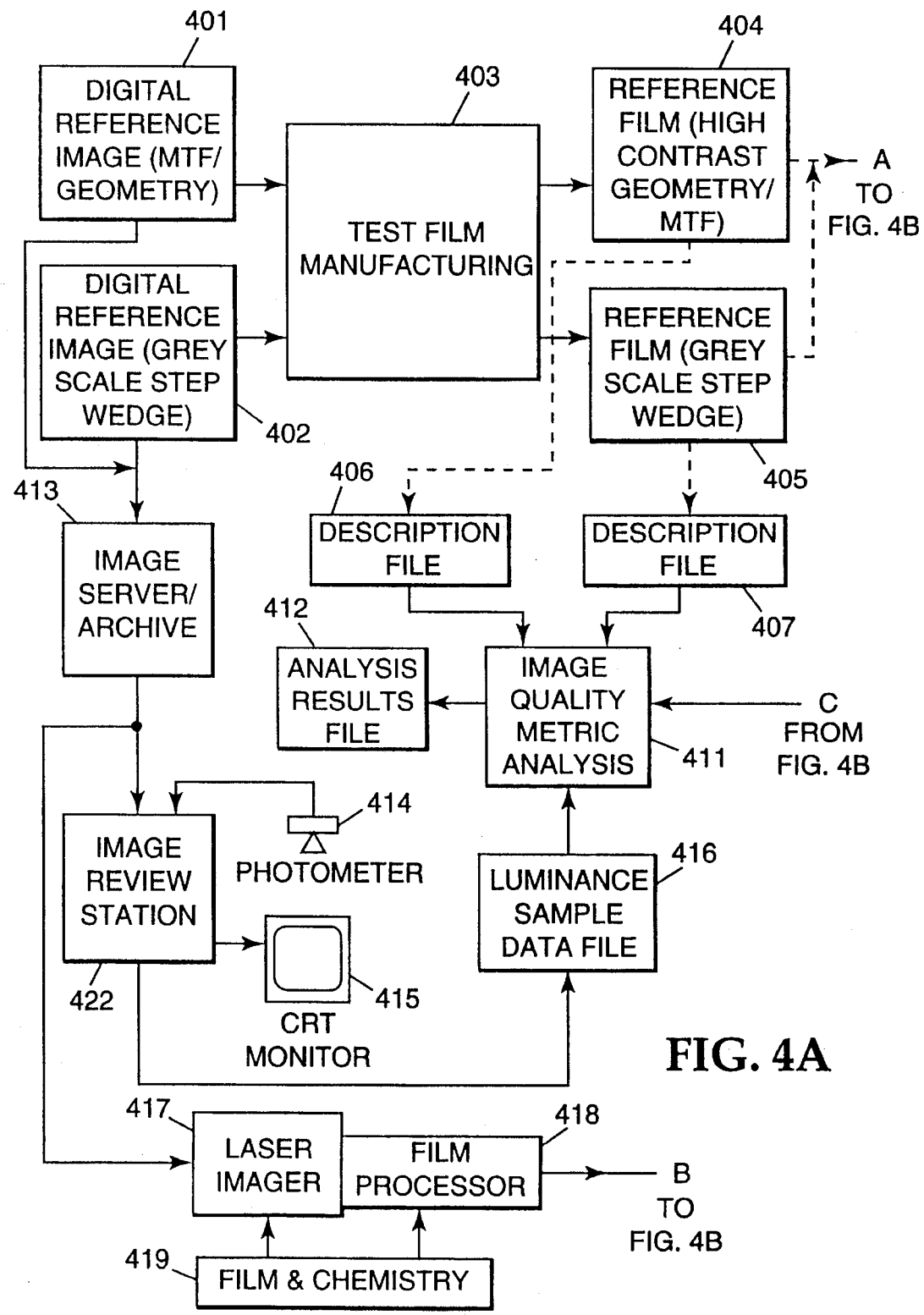
FIGS. 4A and 4B are block diagrams of the automated image quality control system of the present invention applied to an electronic imaging system.
Figure 4B:
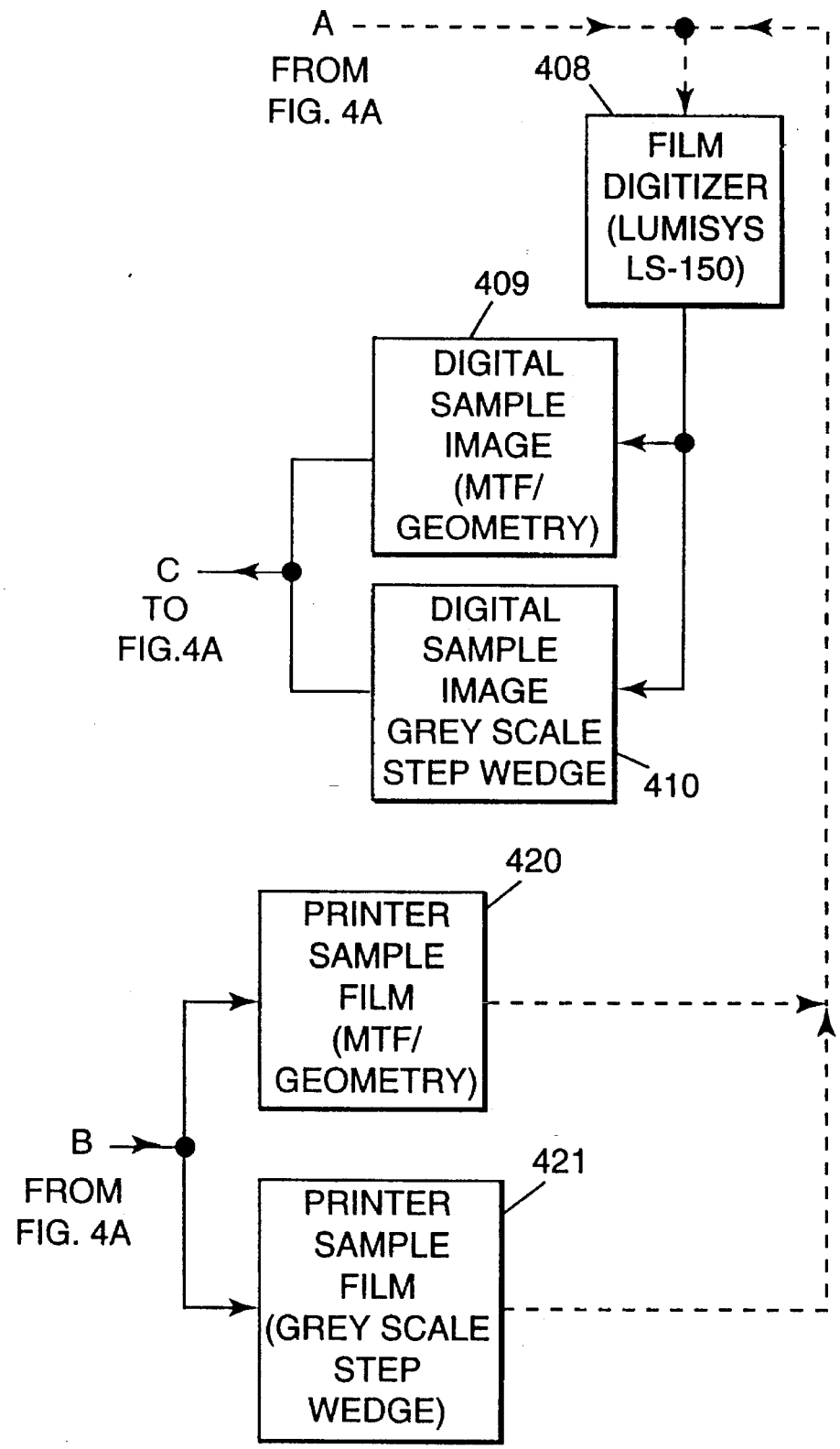

FIGS. 4A and 4B describe the automated image quality control system as it operates in the electronic imaging system. Starting in the upper left hand corner of FIG. 4A, two types of reference images are defined. A digital reference image definition 401 is defined for the testing of the modulation transfer function (MTF) and geometric characteristics within the system. Digital reference image definition 401 is designed to test geometric accuracy and spatial resolution features in the electronic imaging system and corresponds to testing items 4–17 of Table 1. A digital reference image definition 402 is defined to test and measure gray-scale characteristics and corresponds to testing items 1–3 of Table 1.

The image definition used for the measurement of modulation transfer function (MTF) or geometry begins as a data set which describes the specific inch-wise geometries of a digital reference image in the form of a definition file 401. Definition file 401 for the geometric reference image specifies the inch-wise locations of bounding rectangles for the structures shown in FIG. 5. These structures may be rectangles 501, horizontal lines 502, vertical lines 503, diagonal lines 504, horizontal resolution coupons 505, vertical resolution coupons 506, diagonal resolution coupons 507, horizontal single frequency bar 509, vertical single frequency bar 510, etc. The definition file 401 will typically contain the upper-left and lower-right corner locations for a rectangle. For a line, the definition file will typically contain the end-point locations and its width in pixels. In the case of a diagonal line, the definition file 401 will typically contain the upper-left and lower-right corner end-point locations. Coupons 505, 506, 507 are located by defining the upper-left and lower-right corner locations for each coupon. All these location values are in inch-wise coordinates based on absolute corner locations or measured relative to a registration target 508 located somewhere within the reference image (usually the center). The definition file 401 may be generated using industry standard graphics tools to produce the definitions in the form of PostScript (Adobe Systems) graphics definition files, Gerber plotter output and other drawings programs, to give some examples but not by way of limitation.

The definition file 401 for the geometric reference is loaded into the image server 413 of FIG. 4A. The definition file 401 is stored as a binary image of two-valued pixels representing the specifications for an expected image. The location of the structures in the definition file 401 are converted to X-Y digital coordinates for exact pixel locations based on the scan resolution and size selected for this expected image. This expected reference image created from file 401 and stored in image server 413 can later be used to test the precision with which the two valued pixels can be distinguished geometrically and other features shown in Table 1. Expected images represented by the definition files 401 and 402 can then be retrieved and reviewed on image review station 413 to test that component of the system (as described more fully below). The expected images represented by the definition files 401 and 402 can also be retrieved and printed by laser imager 417 to produce printer sample files 420 and 421, respectively, to test that component of the system (as described more fully below).

Vertical resolution performance of the electronic imaging system can be measured and compared to statistics thresholds using a series of vertical bars 505 of black and white to determine the exact spacing, width, separation and pitch. Also, to measure pixel size within the system, a pattern 501 may be used which is perfectly square in the digital reference image as defined in the definition file 401. Thus, if the target 500 has a perfect 1 inch by 1 inch square 501, the electronic imaging system will be tested for its ability to reproduce that exact image. For this type of resolution measurement, the digital reference image defined in definition file 401 does not contain information about the absolute density of the image. Metric analysis of system performance using these expected definitions is described more fully below.

Figure 6:
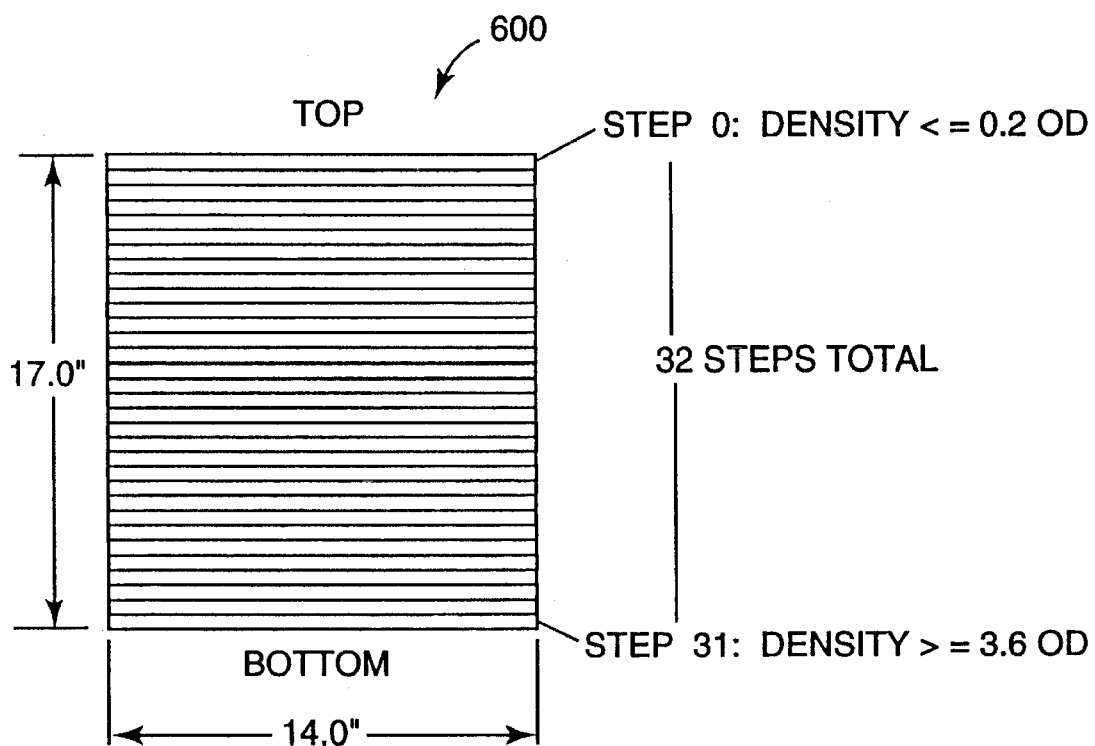
FIG. 6 is an example of the stepwedge pattern for the reference image to test gray scale.

The image used for the measurement of gray-scale system response also begins as a data set which describes the specific gray-scale intensity and locations of the step wedge reference image in the form of a definition file 402. The definition file 402 for the gray-scale reference image specifies the inch-wise locations of the steps and the absolute 12-bit pixel values for the optical density at each step. A diagram of the step wedge reference image is shown in FIG. 6. This definition file 402 is also loaded into the image server 413 for later me as the specifications of an expected image. Definition file 402 may also be produced in a manner similar to the manner used to generate definition file 401 as described above.

In the gray-scale domain tested by the digital reference image defined in definition file 402, geometry is not as important as the actual optical densities. Since it is exceedingly difficult to make a physical test target which simultaneously tests both gray-scale density and geometric resolution (modulation transfer function or geometry), both reference definition files 401 and 402 are needed and two corresponding reference targets 500 and 600 are needed, respectively. In testing system performance regarding gray-scale using the digital reference definition file 402, a wide range of optical densities and low levels of noise must be measured in the physical target and hence, the original physical reference 600 must be of exceedingly high quality to test the optical density required for most medical x-ray film. Specialized medical x-ray films have optical densities reaching 3.7, which is a very, very dense and dark film. Thus, to be able to reproduce such a large dynamic range of optical densities, the acquisition device such as the film digitizer must be capable of reproducing the density scale on a piece of x-ray film. To be able to represent the original medical x-ray images in a gray-scale pixel format, a 12-bit pixel is used to adequately represent the dynamic range of the original optical density.

Physical Reference Films

To ensure the quality of image input retention and display, and to test the performance of system components, the quality control system of the preferred embodiment of the present invention compares the data regarding the untested system's response in handling "real" or physical reference targets or films to that of a known system using the same references. To accomplish this, a physical reference film 404 is generated from the same definition file 401 that is loaded into image server 413 as an expected image definition. Physical reference film 405 is generated from the same definition file 402 that is loaded into image server 413 as an expected image definition. The reference films are used when the input modality is a film digitizer. Different types of targets 404, 405 may be used as described below.

Figure 5:
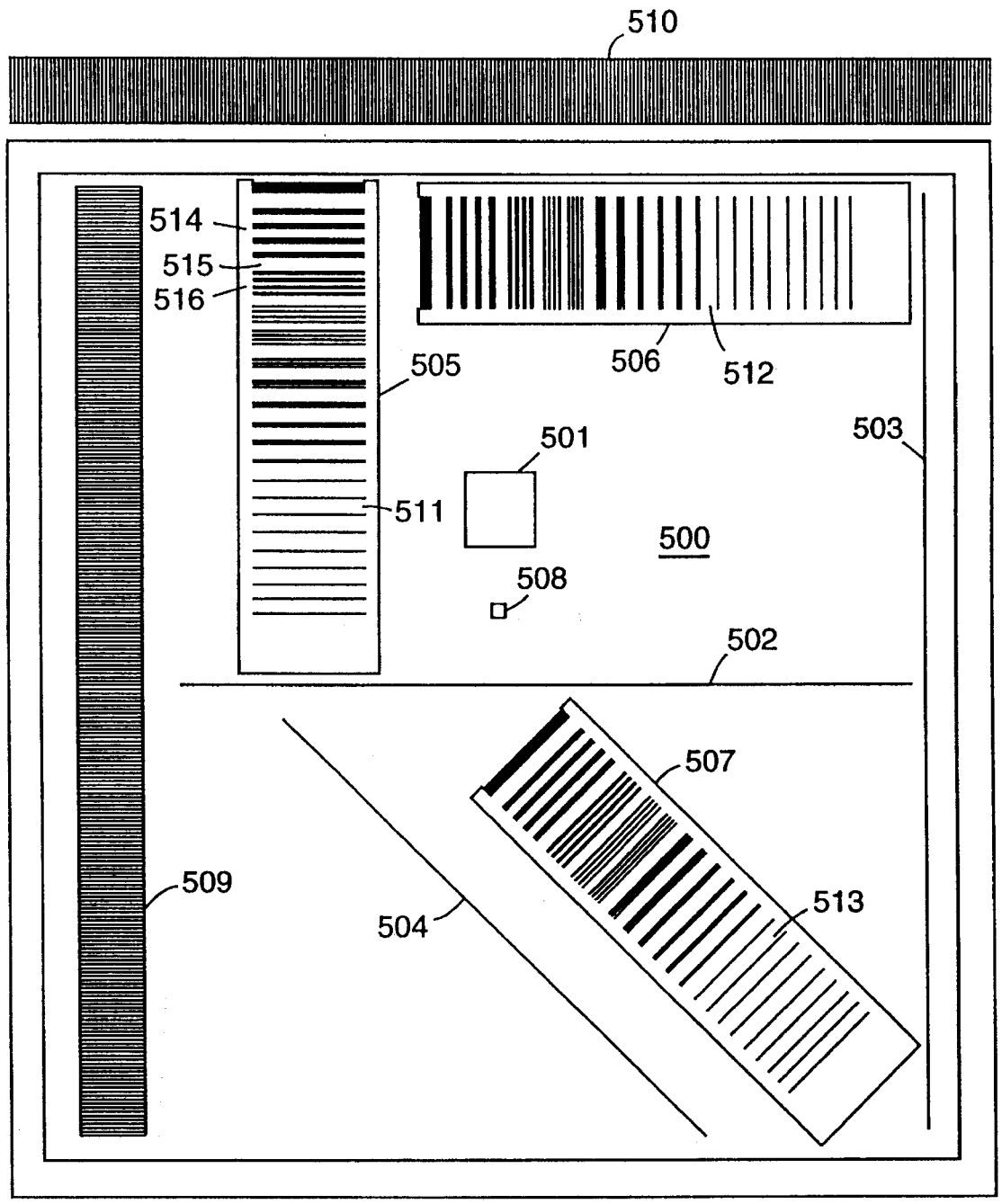
FIG. 5 is an example of a reference image used to test the geometric accuracy of the electronic imaging system.

A specialized test film manufacturing process 403 is used to generate physical reference films 404 and 405 which correspond to the example physical reference films 500 and 600, respectively, shown in FIGS. 5 and 6, respectively. Physical reference film 404 is used to measure system performance for geometric characteristics and spatial resolution response of the system and physical reference film 405 is used to test pixel value integrity response of the system. To accomplish this, physical reference film 404 is generated as a high quality photographic film, such as an x-ray target image of known quality to be input as an original x-ray 211 (as shown in FIG. 2) to test the performance of image acquisition device 10 or other components of the electronic imaging system. The high quality reference images 404 and 405 include features which are sensitive to as many of the potential sources of degradation as possible. As described above, the best possible quality control reference images are used as physical targets that mimic the features to be tested in the system. The physical reference targets are constructed to be compatible with the type of acquisition device used in the particular image acquisition system.

For example, in digital radiography, the target 404 may be imaged onto lead or gold foil and the like, processed using etching processes similar to those used in the printed circuit board industry to produce a target to test for the geometric accuracy in the image acquisition device 10. The target is then used with a digital radiography cassette to input the sample images when the image acquisition device 10 is a digital radiography cassette scanner. Also, for a gray-scale target, conventional metal step wedges can be used as the target 405 which then can be x-rayed using the digital radiography input device as a sample or target of known gradient density.

In another example, when the image acquisition device 10 is a film digitizer 210, geometric reference images can be produced by plotting the geometric patterns using high-precision components typically used for printed circuit board artwork generation. These geometric plots are then photographed onto conventional or x-ray film to produce the sample targets 404. For gray-scale targets, conventional metal step wedges can also be used as a gray-scale target which then can be x-rayed onto film to produce an x-ray sample target 405 of known gradient density. Gray-scale patterns can also be made using laser imagers or by direct exposure onto conventional or x-ray film using step and repeat exposure techniques.

For other scanning modalities used as the image acquisition device 10 such as MRI, CT scan or ultrasound, special purpose three-dimensional test phantoms may be used. The example, a phantom having a plurality of test tubes spaced at fixed locations relative to one another and containing gradients of liquid densities may be used to measure the performance of the MRI scan input device.

For optimal testing and quality control of the electronic imaging system where a film digitizer is used as the acquisition device 10, extremely accurate reference films 404 and 405 must be produced from definition files 401 and 402, respectively. This accuracy requirement is to ensure uniform measurement of the system components for metrics calculation. Thus, one of the keys to the present invention is the production and use of extremely high quality digital reference images.

In all of the examples described with the present invention, the number of films, targets or phantoms, while shown to be two, may be of any number. It is always desired to limit the number of phantoms so as to minimize the time required for acquisition and hence the overall quality assessment.

Production of Geometric Reference Film

FIG. 5 is an example of a reference image used to test the geometric accuracy of the electronic imaging system. The geometric reference film 500 of FIG. 5 corresponds to the reference film or target 404 used to test high contrast geometry and MTF (modulation transfer function). The digital reference film or target 404 is produced in the preferred embodiment using conventional photolithography systems such as the type used for printed circuit artwork. In this fashion, perfectly parallel lines drawn as long as 1 meter which deviate by as little as 0.1 mm are easily generated for measuring perfect size precision.

The reference film of FIG. 5 contains a number of high contrast items sufficient to measure each of the geometric features of Table 1. There are two sets of single frequency bars, 509 and 510, extending in both the vertical and horizontal axes of the image. These are analyzed by the metric analysis described below to test the uniformity of the bar width and spacing between adjacent bars to determine scan velocity uniformity in these directions. The analysis utilizes statistics derived from run length calculations on bar patterns. These statistics coupled with the previously stored knowledge of the bar patterned pitch leads to direct computation of the pixel size and aspect ratio. The rectangular border bars 511 as well as the fine vertical and horizontal lines, 505 and 506, allow for determination of the start and end of scan uniformity and laser beam wobble statistics. Also included are precisely straight edges extending the full width 502 and length 503 of the image, rectangle 501, diagonal line 504, horizontal resolution coupons 505, vertical resolution coupons 506, diagonal resolution coupons 507, horizontal single frequency bar 509, vertical single frequency bar 510, etc.

The requirements for reference film 500 require that the geometric features be placed on a film with stringent positional accuracy and only need to be bi-tonal. The features for the image are generated on a graphics art plotter such as a gerber scientific plotter for creation of the original image. The image is transferred to film using the same equipment developed for the printed circuit board art work industry. A flat bed step and expose machine, such as those from Gerber Scientific, is ideally suited to production 403 of the geometric reference film 404.

Production of Gray-Scale Reference Film

In order to generate a gray-scale reference film 405, a continuous tone imaging process is used. The preferred approach is to first generate a master step-wedge in which unexposed x-ray film is exposed in a stepwise fashion with multiple exposures for a certain number of milliseconds to create a stairstep pattern of optical image density exposures on the x-ray film. Thus, one small strip of the unexposed x-ray film is exposed for a fixed period of time. Exposure is stopped and a next line increment of the x-ray film is exposed and both the previously exposed increment and the presently exposed increment are then exposed to increase the amount of exposure. This step and repeat process thus exposes the very first line a multiple number of times and the very last line only once. The result is a stepped gray-scale with no scan line artifacts. The crispness of the gray-scale master reference film 405 is determined by the sharpness and opacity of the edge that is used to produce the master.

The relationship of the density versus the step position of the gray-scale image must be controlled very carefully since the master image is going to be used to produce a plurality of other x-ray films. This is accomplished by laying the master on top of another unexposed x-ray film and expose it to a uniform illumination using a contact exposure process. This results in a duplicate of the master with uniform density steps of exposed areas. Since the optical density is a logarithmic function, the exposure characteristics and sensotometry of the original is nonlinear. Thus, the density steps on the first generation master are not linear. To produce a stepwise function of linear optical density of the film, the speed characteristics of the film, and the exposure times must be properly calculated to produce a linear result. The resulting reference film 405 for gray-scale stepwedge is a monotonic density step function.

The reference film 405 generated to test the gray-scale is formed using a step wedge pattern such as that shown in FIG. 6. A stepwedge master film 600 is used to make contact copies as described above. The copies are then used for testing of the quality assurance of the components of the electronic digital imaging system. In the preferred embodiment of the present invention, the copies are x-ray image film measuring 14" wide × 17" high (35 cm × 43 cm). Double emulsion film is patterned using a 32 step wedge each horizontally aligned across the full film width. As shown in FIG. 6, the first step (step 0) has an optical density of less than or equal to 0.2. The last step (step 32) density should be greater than or equal to 3.6. Each nominal density step therebetween should be approximately 0.11. Step uniformity across the film width should be plus or minus 0.1. The nominal step height is 0.53" or 1.35 cm. measured across the height of the film.

Descriptor Files

When the reference films 404 and 405 are produced and ready for use for input into the electronic imaging system, a description file is made to calibrate the reference films 404 and 405. Each description file 406 and 407 contains characteristics of the reference films 404 and 405 as part of the calibration for that particular electronic imaging system. This is necessary since the transfer of the master digital reference images through the transfer processes 403 to produce the reference films 404 and 405, respectively, is not always uniform. The temperature of the film developing process, the particular sensitivity of the film between different batches, and the requirement of a very high optical density for this film necessarily will produce variations among the reference films. Because of these variations, the individual reference films 404 and 405 must be calibrated to the particular system and corresponding description files 406 and 407 are produced. The description file 407 describes the density of each step, the width of the step, and the uniformity of each step for the step wedge reference film 405. Several measurements of the reference films are produced and an array of values for these different points on the reference film are stored in the reference files.

For the description file 406 of the reference film 404 to measure high contrast, geometry and MTF, no attempt is made to calibrate the geometry or MTF target. What is included instead is a description of the bar pattern pitches, widths and sizes of any of the features on the reference film corresponding to the definition 401. This is in terms of XY locations of features rather than density measurements of gray-scale information such as found in description file 407 for reference film 404.

The step of creating the reference films 404 and 405 and the corresponding description files 406 and 407 respectively is done once and the reference films and description files are stored for later calibration and measurement of the performance of the electronic image system.

Calibration

The electronic imaging system is setup, calibrated and tested in the factory. Initial test data is saved for later trend tracking (preventative servicing). The reference films 404 and 405 and their corresponding description files 406 and 407 always remain with that particular electronic imaging system for quality testing and calibration purposes. The reference films are input into the system using film digitizer 408, which in the preferred embodiment of the present invention, is a Lumisys model LS-150 film digitizer. The reference images 404 and 405 can then be scanned in and digitized during any test and calibration time to measure the performance of the digitizer 408 over the life of the system through the use of the image quality metric analysis software system 411 to produce analysis results files 412, which indicate the performance of the digitizer, as described more fully below.

The image quality metric analysis 411 is used to measure the components of the electronic imaging system described above in connection with FIGS. 1 and 2, namely: the image acquisition devices 10, the image display devices 20, the image storage devices 30, and the image hard copy devices 40. All four components of the electronic imaging system can be measured and degradation of the image quality and performance of these components can be analyzed.

Spatial Resolution Test Features

Spatial resolution is a measure of the ability of an image manipulation component to preserve image sharpness. It is also known as the point spread function, or in the frequency domain, as the modulation transfer function (MTF). The former is the well-known two-dimensional impulse response of the system while the latter is the magnitude of the Fourier transform of the point spread function These are equivalent means of representing image sharpness but MTF is the most frequently-used measure. The MTF is the continuous measure of the contrast response of the system to a range of spatial frequencies. In practice, the MTF is sampled by computation of the contrast response to a set of discrete spatial frequencies. By use of a set of test patterns containing a number of single frequency bar patterns 509, 510 as shown in FIG. 5, the contrast response can be obtained by observation of the histogram characteristics sampled around each bar frequency. The set of numbers obtained is then a sparse sample of the continuous MTF and a quality assessment can be made by examination of the contrast roll-off characteristics of the MTF.

In the preferred embodiment of the present invention, the MTF must be calculated from a set of pixel values corresponding to image transmission, not density. This conversion takes place during the feature extraction process described above in conjunction with FIGS. 4A and 4B. The preferred test features for this measure are shown as three sets of multi frequency bar pattern arrangements 505, 506 and 507 as shown in FIG. 5. The multi frequency bar patterns are oriented vertically, horizontally, and 45 degrees off axis. This allows the system to sample the MTF at the three most important rotation angles where a scanned image device is most apt to incur MTF loss.

Pixel Value Integrity Test Features

To test for pixel value integrity, an image containing a broad range of densities is required such as that described above in conjunction with FIG. 6 which corresponds to reference film 405 described above in conjunction with FIG. 4A. A sufficient number of sample points on reference film 405 is required to reveal any nonlinearities over small ranges of input values. To measure the uniformity of response, the input regions of equal density should be as uniform as possible. The test features for this form of quality monitoring is accomplished using the stepwedge pattern as described above in conjunction with FIG. 6. The stepwedge of FIG. 6 has a dynamic range that equals or exceeds that of the component under test. A wedge with 32 steps and a maximum density of at least 3.6 OD is used in the preferred embodiment to the present invention.

To reduce the absolute accuracy requirement and repeatability of the stepwedge manufacturing process, each reference film 405 must be independently characterized. This information will then be conveyed to the metrics computation process in the separate descriptor file 407 described above in conjunction with FIG. 4. The descriptor file 405 is unique to each reference film and accompanies each reference film as it is stored in memory for use by the preferred embodiment of the present invention.

Image Quality Metrics Analysis Examples

By way of illustration, but not by limitation, the present invention is capable of measuring the "laser beam wobble" in a laser-based film digitizer. In such a digitizer, a laser spot scans continuously across the width of a film while the film is moved in a path orthogonal to the laser scan direction. Ideally, the trajectory of the laser spot across the film should be a straight line. However, the opto-mechanical system used to scan the laser beam can make the trajectory something other than straight. This aberration can occur due to such physical manifestations as warp in the mirror surfaces, misalignment of the mirror segments (if a rotating polygonal mirror is used), lens distortion and bearing run out or vibration in the moving components. The result will be that the straight edges in the reference image will be converted to curved lines in the sensed or printed image. To quantify this distortion, the preferred embodiment of the present invention produces a single number output from the metrics analysis which is a measure of the total deviation from straightness in the sample image due to this effect.

In the preferred embodiment of the present invention, this metric first isolates all of the edge pixels in a sample image resulting from a scan of a perfectly straight line or edge oriented parallel to the scan direction of the reference image as shown as the border of FIG. 4A and 4B. The result is to establish an image processing procedure including vertical gradient, thresholding, morphological dilation and thinning. The result will be a set of linked binary edge pixels that trace out the trajectory of the laser scan. From this array of pixels, the system extracts the set of Y-coordinates for each pixel. A classical statistical analysis procedure known as linear regression is then applied to this set of coordinates. This procedure derives the parameters for a straight line which best approximates the trajectory path with the goodness of fit measured by a minimum mean-squared error criteria. This procedure also automatically accounts for any rotation that may be present in the reference film at the time it is scanned. As a result, a statistical quantity "standard error" which is an RMS (root mean square) measure of the total deviation in the sample population from the best approximation. This value can then be tested against a preset threshold value to give a go/no-go decision as to the acceptability of any laser beam wobble that may be present.

The same technique is applied to the start/end of scan geometric metrics as well as the density response linearity metrics during the acquisition and printing functions of the electronic imaging system. The application of statistical measures for the other two geometric metrics differs only from the image quality metric analysis only in the quantities used for the regression analysis, such as pixel coordinates or pixel values.

Other metrics, described more fully below, utilize some form of statistical measure such as mean, standard deviation, or variance. In all cases, the result is a small set of numbers which can be used in a simple go/no-go test decision to perform image quality assessment on the operation of the overall system.

Image Acquisition Quality Metric Analysis

Referring once again to FIGS. 2 and 3, image acquisition device 10 is used to input a digitized image into the system. The reference films 404 and 405 are scanned by digitizer 408 to produce digital sample images 409 and 410, respectively. The digital sample images 409 and 410 are analyzed by the image quality metrics software to locate specific regions of interest and to compute measurements for each region of interest. The measurements are then compared to stored threshold values for each region of interest to determine if the system is performing at the proper performance level.

An example of a geometric/MTF reference film 404 is shown in FIG. 5 as reference film 500. This film contains a number of regions of interest, the locations and descriptions of which are described in description file 406. The image quality metrics analysis software 411 first locates the registration target 508 to compute an offset vector to locate the bounding rectangles and other regions of interest in the scanned digital sample image 409. The analysis software 411 knows to begin looking for the small black square registration target 508 in the center of the image using standard feature recognition routines. A large region of interest is assigned to the center of the digital image 409 and a histogram is extracted and searched to locate the valley in what should be a bimodal histogram. The valley indicates the density which optimally separates the dark registration target from its surrounding light background. This density of the valley is used as a threshold to discriminate registration target pixels. The result of the thresholding is a binary image which is further analyzed to extract the centroid of the target 508. This is accomplished using either repeated erosion or row/column slicing.

The X and Y coordinates of the centroid of target 508 in the binary image of the digital sample image 409 is used to map onto the true center in the original image 404 as described in description file 407. This mapping first tells the analysis software 411 how much the image is shifted left or right and allows the analysis software 411 to assign an offset vector (skew) for the location of the other regions of interest in image 409. Locating the other regions of interest is a prelude to computing metrics of the scanner 408 performance for each region of interest to allow the metrics of Table 1 to be computed.

There is a likelihood that the physical reference film 404 was slightly rotated when it was scanned by film digitizer 408 resulting in a rotation of the image 500 as it was digitized into digital sample image 409. This rotation is of little import since the metrics are designed to operate in the presence of rotation and to compute their respective results independent of rotation. For example, one of the statistical techniques in measuring the performance of the film digitizer or scanner 408 is to measure the linear scanning ability based on lines 502, 503 and 504. The endpoint pixels of the scan lines 502, 503 and 504 are located in the image file 409 and a best fit linear regression is performed on the pixel locations. For example, for vertical line 503, a best fit linear regression is performed on an array of the Y-coordinates of the pixel locations. The metric analysis software then performs a best-fit line to the data set which makes the analysis rotation independent.

For the analysis of run lengths in the in-scan or cross-scan direction, features 510 and 509 are used respectively. A very long and narrow region of interest is defined within the bar spacing regions so that the region of interest stays completely within these features. Within these regions of interest, there is no concern for rotation since only the peaks and the standard deviation between the peaks representing the lines within features 510 and 509 are analyzed. The standard deviations will indicate the linearity of the scan velocity in the direction analyzed.

The modulation transfer function within coupons 505, 506 and 507 are also rotation independent. These coupons 505, 506 and 507 are used to test the resolving ability of the film digitizer 408 and are analyzed similar to the technique described above for the analysis of run lengths. The bounding region of interest is placed completely within the coupons to do the histogram analysis on the resolution bars of coupons 505, 506 and 507. The spaces between the bars 511, 512 and 513 for coupons 505, 506 and 507, respectively, are purposely placed to allow small regions of interest to be placed between resolution patterns. For example, resolution pattern 514 is designed to measure 0.2 line pairs per mm. vertical resolution in coupon 505. Resolution pattern 516 is designed to measure 0.4 line pairs per mm vertical resolution in coupon 505. Space 515 between resolution patterns 514 and 516 is designed to allow a region of interest to only cover a portion of the horizontal bars of resolution pattern 514 without including any portion of resolution pattern 516 or the edge of coupon 505. Thus the test pattern features of reference film 500 is specifically designed to be rotation independent. There are, however, features 501, 502 and 503 which can be used to measure the amount of rotation from the definition file description 406 if measurement of rotation is a metric of interest.

Streak Detection Process

As a pre-cursor to the pixel value integrity tests that are performed upon the gray scale step wedge reference film 405, a streak detection process is first undertaken. An example of a gray scale step wedge reference film for digitizer or laser imager testing is shown in FIG. 6 as reference film 600. This film object contains a number of horizontally aligned uniform density steps arranged with increasing density down the vertical axis of the film. The streak analysis process is used to detect the presence of any vertically oriented disturbances in acquired or printed images. These disturbances arise due to several problems:

1) Contamination of the folding mirrors used in a swept beam laser film digitizer or computed radiography system;
2) Contamination or obstruction of line illuminators used in CCD based film digitizers;
3) Mis-calibrated or failed pixel sites on CCD's used in a CCD-based film digitizer;
4) Contamination of rollers used in transport of film through either a film digitizer, laser imager, or film processor;
5) Mechanical damage (scratching) of a film due to burrs or out of alignment mechanical guides or deflectors used in a film transport path.

All of these sources of streaks produce a sensed density anomaly in the form of a continuous or periodic vertical (or nearly vertical) line which may be darker or lighter than the surrounding background. The purpose of the process is to determine if such streaks are present (detection), and if so, to classify them in terms of their width, position on the image, and whether they are above or below the background level. The occurrence of any streaks will usually be construed by the procedure which invokes the streak analysis to be a fatal error, in that subsequent pixel value tests or calibration should not be carried out until the came of the streaking has been removed. The information used to classify a streak can be used by higher level software (such as a rule based AI program) or by skilled technicians in locating the source of the streaking.

Two different approaches to streak detection are utilized, depending upon the type of acquisition modality. Both of these use the concept of background estimation and subtraction to produce an image object which is then analyzed for the presence of vertical anomalies having some minimum extent along the y-axis of the image. The background extraction algorithms utilize conventional linear convolution and/or morphological filtering.

The first streak detection algorithm uses a two-pass 2-D background estimation, while the second one utilizes column summation to reduce the problem to 1-D, thereby saving considerable processing time. The later approach, while inherently faster, could fail to detect a streak if there is any substantive rotation in the film under test as it is being digitized. This approach is restricted to use with a film digitizer where it is known in advance that the maximum rotation in the acquired image is small. For CR, or systems with less control of the rotation during acquisition, then the slower, but rotation independent, 2-D background subtraction process must be utilized.

The anomalies are detected first within each step of the gray scale step wedge, using a test for either the pixel value deviation above background or the instantaneous slope (horizontal gradient) to determine candidate anomalous regions. The total y-extent of each candidate region is measured, as well as the width of a potential streak, and its "color" or polarity relative to the image background. All of this streak classification information, including the total number of streaks encountered is saved as a result for the purposes stated above. Anomalies which do not satisfy a minimum length criteria are considered to be discrete anomalies. A count of these is also maintained as an indicator of the overall cleanliness and random scratch content in the reference film so that reference quality can be monitored and the reference replaced at such time as the discrete anomaly count exceeds a pre-determined threshold.

Example of Registration of an MRI Image

When the acquisition modality is one of the common 3-D volumetric imaging systems such as MRI, CT or the like, a registration process to identify any rotation in the coordinate space is especially critical to the successful application of predetermined region-of-interest processing. To accomplish this task, one can rely either upon the existence of identifiable targets in commercially available phantoms (such as those from Cone Instruments) or preferably, to design into custom phantoms 3-D objects which when imaged produce pixel sets which are amenable to the form of automatic image processing and feature extraction discussed here. A typical MRI phantom used for MTF and geometric distortion measurement will usually have a number of circular inserts spaced radially around the axis of a cylindrical volume. Each insert will have a number of vanes or target pins spaced so as to simulate a different spatial frequency. The unknown in such an acquired image will be the angular rotation of the cylinder. Ideally, an object to be used for registration would be embedded in the plane of the volume of interest which has a structure that is significantly different from the test objects. For instance, if the MTF test patterns utilize circular elements, than the registration target should be a rectangular (or at least rectilinear) object. It should also be a size or density difference so that when an appropriate pixel value or morphological (shape sensitive) filter is applied to the resulting image, a clear discrimination between the registration target and the test features is obtained. Once the pixel coordinates of the registration target have been determined, then the orientation of the test features can be derived using a priori knowledge of the spatial relationship between all of the features in the phantom. The output of the registration process would again be an offset vector, now a 3-tuple, which is used to adjust the application of any preset regions of interest for further quality testing.

Image Hard Copy Quality Metric Analysis

Referring once again to FIGS. 2 and 3, image hard copy device 40 is used to output a digitized image of the system. The image quality metric analysis tests the characteristic of the hard copy device 40, which in the preferred embodiment of the present invention, is a laser imager 207. Referring to FIGS. 4A and 4B, the testing of the performance of the laser imager 417 (corresponding to laser imager 207 of FIG. 2) is a closed loop analysis requiring the use of film digitizer 408. For this reason, the film digitizer must be calibrated and its performance measured before the performance of the laser imager 417 can be measured.

To test the output of the laser imager 417, stored digital reference images corresponding to the expected images defined in files 401 and 402 are retrieved from the image server 413 (corresponding to the disk storage system 204 of the image storage device 30 of FIG. 2). The laser imager 413 will produce printer sample films 420 and 421 of the expected reference images defined in definition files 401 and 402, respectively. The laser imager exposes x-ray film or the like and processes the film through film processor 418, which is an integral part of the image hard copy device 40. The printer sample film 420 allows for the measurement of the MTF and geometry characteristics of the laser imager. Printer sample film 421 allows for measurement of grayscale characteristics of the laser imager 417. Sample images 420 and 421 are scanned back into the system using film digitizer 408 in a closed loop fashion shown in FIG. 3. Film digitizer 309 scans in printer sample film images 420 and 421 for input into the image quality metric analysis 411. The results of the analysis are stored in the analysis results file 412.

The values of the image quality metrics are tested against predetermined threshold values to determine if there has been any degradation in the hardcopy generation process. The degradation of the digitized images 409 and 410 corresponding to printer sample files 420 and 421, respectively, due solely to the film digitizer is compensated for during the image quality metric analysis 411 if the digitize was first calibrated and its performance was measured before testing the performance of the laser imager 417.

Image Display Quality Metrics Analysis

The testing of the CRT monitor of image review station 415 corresponds to the image review stations 212a–212c of FIG. 2. The measurement of the performance of a CRT monitor is difficult due to the wide variations in phosphor degradation, linearity, horizontal phase, width, vertical sizing, pincushion patterns and ringing. With the wide variation in geometric performance of CRT monitor 415, a complete performance measurement is difficult. Within the realities of the use of an electronic imaging system, it is more important to measure the gray-scale performance of such CRT monitors 415 than it is to measure the geometric performance characteristics. Thus, in the preferred embodiment of the present invention, only gray-scale performance of the CRT monitor is performed. This is primarily due to the fact that the geometric display characteristics of CRT monitor 415 do not degrade in a slow linear fashion. Most often, the degradation of a CRT monitor, and the geometric characteristics, is on a grand scale such that tremendous shrinking or distortion occurs all at once. This is typically due to a failure of an electronic component within the CRT monitor. More subtle changes in the geometric characteristics of the CRT monitors are not as much of a concern, especially in the medical industry, since the monitors are rarely used to infer actual physical size of the image that they are displaying. Even relative sizing of the portions of the image are typically not relied upon. For relative sizing of portions of an image, a hard copy x-ray image or the like is produced.

Photometer 414 is used to measure the gray-scale characteristics of CRT monitor 415. The photometer 414 is attached to the face plate of the CRT monitor at a predesignated location in order to measure the gray-scale performance. The result of the photometer readings from photometer 414 are quantified and stored in a luminance sample data file 416 for use by the image quality metric analysis routines 411 for comparison against a predetermined digital value-to-luminance function. The results of this comparison can be used to determine the performance of CRT monitor 415 in the gray-scale domain and the results of this analysis is stored in analysis results file 412. The results are also used to perform calibration of the display system by manipulation of the display LUT (Look-Up Table).

Hardware Look Up Table Descriptions

Look Up Tables are utilized within the electronic imaging system of the present invention to perform conversion of an incoming pixel data set to an outgoing pixel data set so as to achieve a desired transfer function for a particular system component. In so doing, multiple objectives are achieved including calibration, matching and adaptation to a variety of pixel value representations. For example, the CRT display LUT (Look Up Table) is used to match the CRT contrast and brightness to the film density of the original film. The printer CLUT (Contrast Look Up Table) is used to match the printed film density to that of the original film. The digitizer LUT is typically used to fine tone the instrument's calibration and remove any non-linearity in the (usual) density-to-density transfer function.

Figure 7:
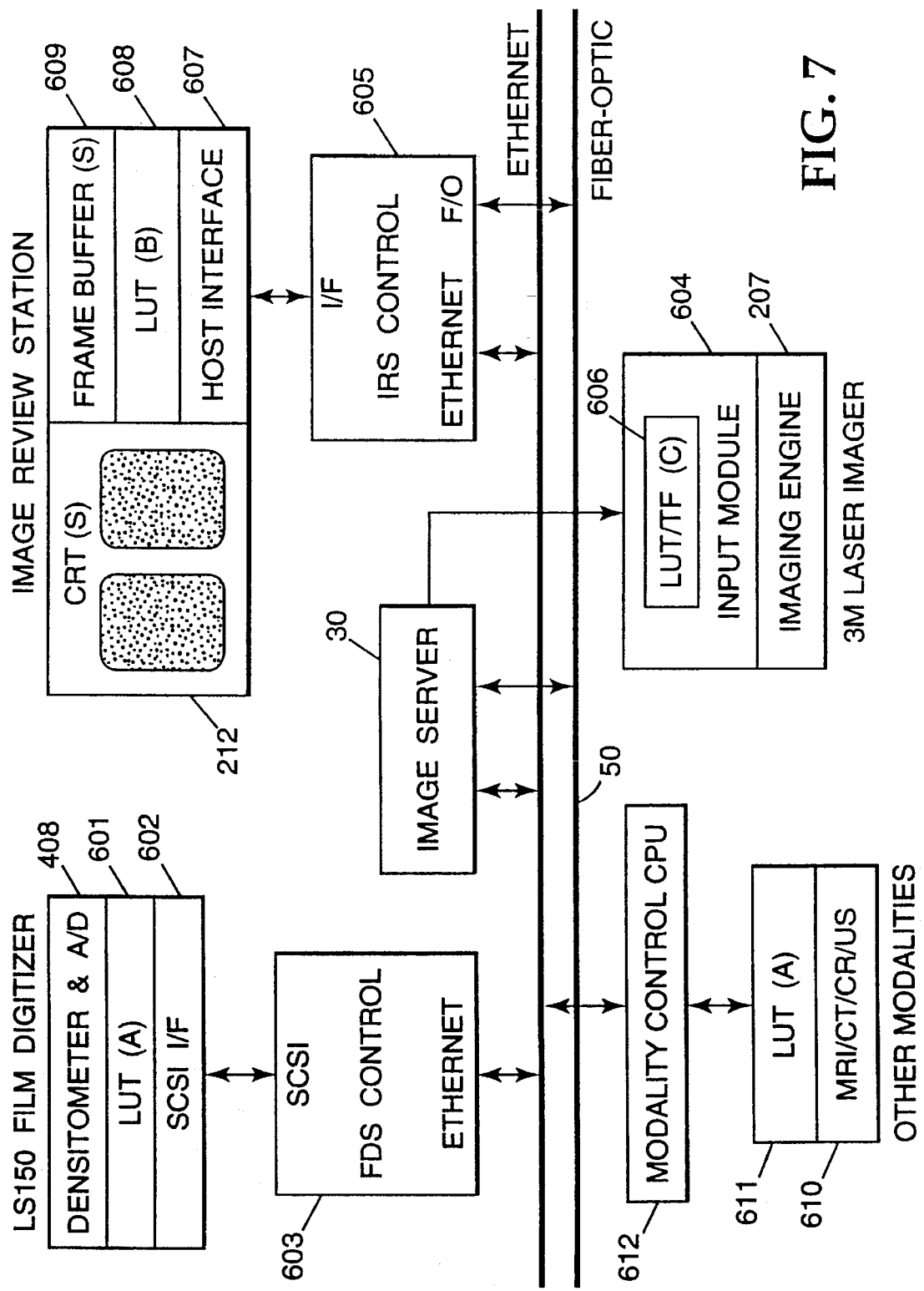
FIG. 7 is a block diagram of a portion of the automated image quality control software components of the preferred embodiment of the present invention showing the LUTs.

FIG. 7 shows the relevant portions of the automated image quality control system for the electronic imaging system of the preferred embodiment of the present invention system where LUT's are used to transform pixel quantities. There are three LUT's in the basic system: LUT A 601, LUT B 608 and LUT C 606. The nomenclature used to describe the LUT input and output values is shown in Table 2.

TABLE 2

| | LUT Input and Output Nomenclature | | |
|---|---|---|---|
| Input | LUT | Output | Location |
| MOD [0:11] | LUT A | MPV [0:11] | Film Digitizer Output Stage |
| MPV [0:11] | LUT B | DPL [0:7] | CRT Graphics Controller |
| MPV [0:11] | LUT C | IPE [0:11] | Imager Input Module |

LUT A 601 is incorporated in the Lumisys film digitizer 210. LUT A receives a 12 bit quantity MOD[0:11], corresponding to the Measured Optical Density output by the A/D converter of the Lumisys apparatus. This value is calibrated by Lumisys to represent directly the film density as an equivalent number of milli-OD (0.001 OD) units, with a maximum usable output of 3600, corresponding to 3.6 OD (see FIG. 8). As a 12 bit unsigned integer, values for MOD up to 4095 are possible. The output of LUT A is also a 12 bit integer, which is denoted as MPV[0:11], for Measured Pixel Value. Images consisting of an array of MPV integers are what are then stored within the Image Server 30 of the system. It should be noted that LUT A may also be equivalently a part of any of the other image acquisition devices, such as a CR or MRI machine.

LUT B 608 is located in the display driver/frame buffer hardware of the Image Review Station 212. Its input is the MPV[0:11] array from the image server, and its output is the Display Pixel Luminance, which is denoted as DPL[0:7]. LUT B 608 is typically updated by the control CPU 213 of FIG. 2. LUT B simply compresses the 12 bit input data to 8 bits of CRT Luminance intensity. The content of LUT B will determine the window and level of displayed data, and how that data is mapped to CRT gamma and perceived brightness levels.

Other input modalities can be used in the preferred embodiment of the present invention which utilize a LUT table. For example, input modality 610 may be magnetic resonance imaging (MRI), computed tomography (CT), computed radiography (CR), ultrasound (US), and others. The LUT (A) 611 used with these modalities is as described above and operates in the same manner through the modality control CPU 612.

LUT C 606 typically resides on the Laser Imager 207. It is used to map a particular digital image modalities' pixel values into the appropriate film exposure values. Thus, the input to LUT C is the array MPV[0:11], while its output is another 12 bit value of Imaged Pixel Exposure, denoted IPE[0:11]. It may also be implemented either in hardware or software as part of control CPU 201 of FIG. 2.

Figure 8:
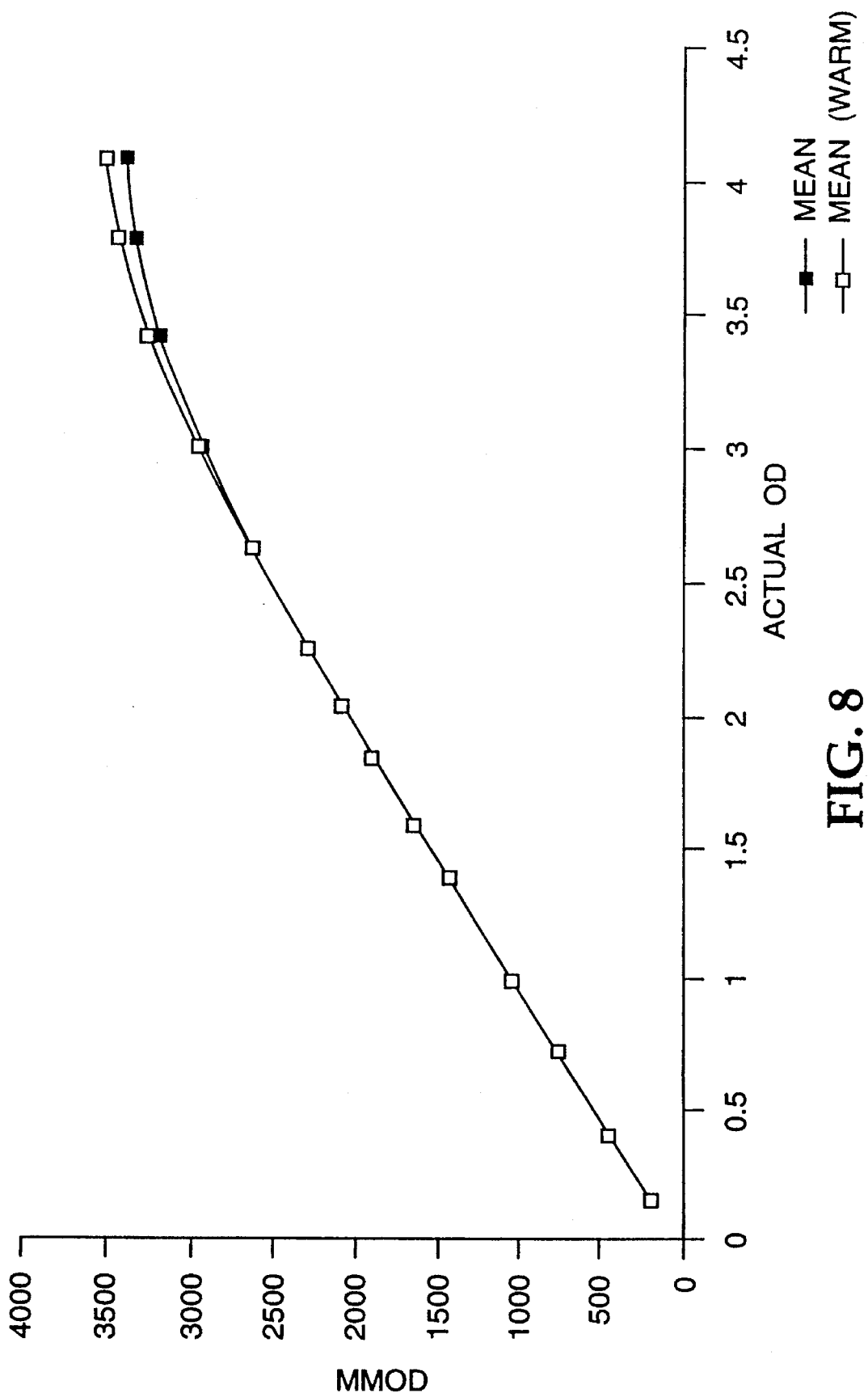
FIG. 8 is a graphical representation of a typical density response curve for the Lumisys model LS150.

It should be noted that the Lumisys Film Digitizer (selected for use in the preferred embodiment of the present invention) can sustain some calibration drift resulting in a somewhat nonlinear film density response. FIG. 8 shows a typical density response curve for the Lumisys model LS150. The unit has slightly excess gain for densities up to about +/−6 percent nonlinearity. LUT A 601 in the film digitizer 408 is loaded with the values shown FIG. 9 to provide compensation for the residual nonlinearity in any given unit. The LUT A 601 is calculated during calibration (as described more fully below) and has the general form shown in FIG. 9. This version of LUT A in FIG. 9 preserves the modalities' native pixel representation (milli-0D units).

Figure 9:
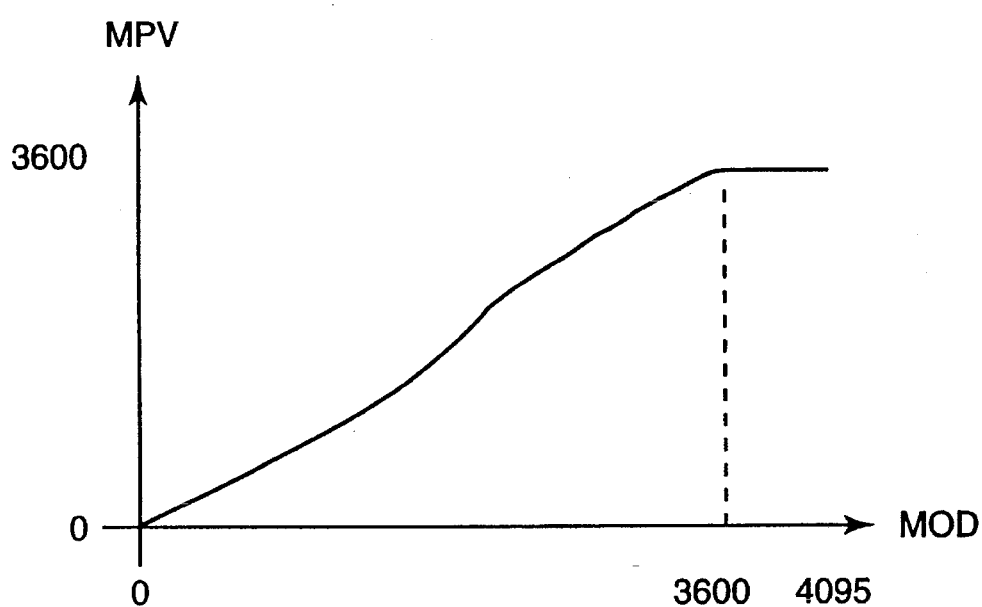
FIG. 9 is a graphical representation of the calibrated values for LUT A.
Figure 10:
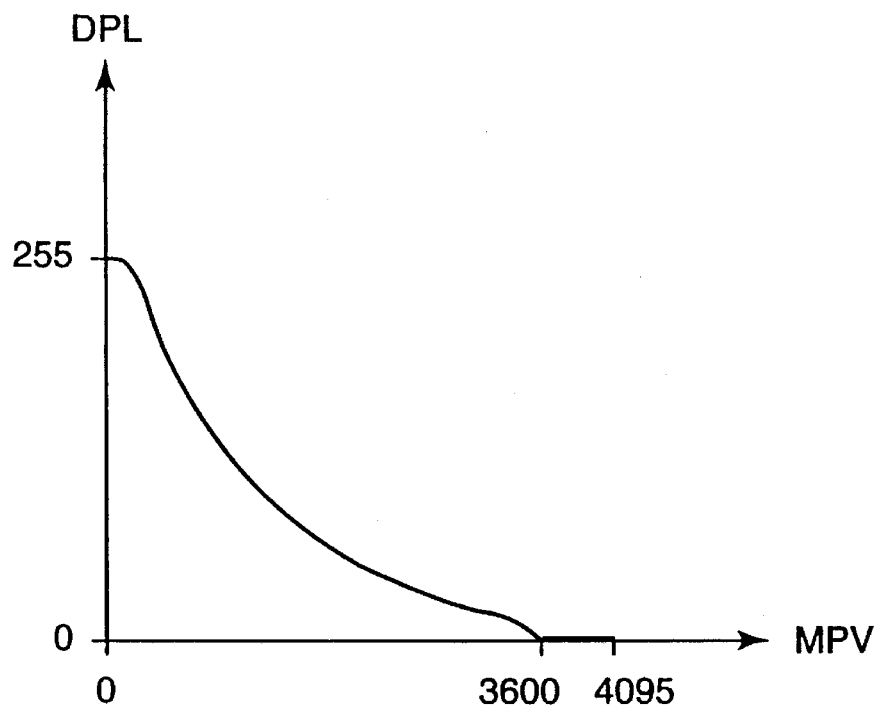
FIG. 10 is a graphical representation of the calibrated values for LUT B.

In conjunction with LUT A of FIG. 9, LUT B would be required as shown in FIG. 10. LUT B of FIG. 10 is calculated during CRT calibration based upon the measured CRT gamma characteristics, the pixel value representation of the source and the desired CRT luminance-to-source perception transformation.

Figure 11:
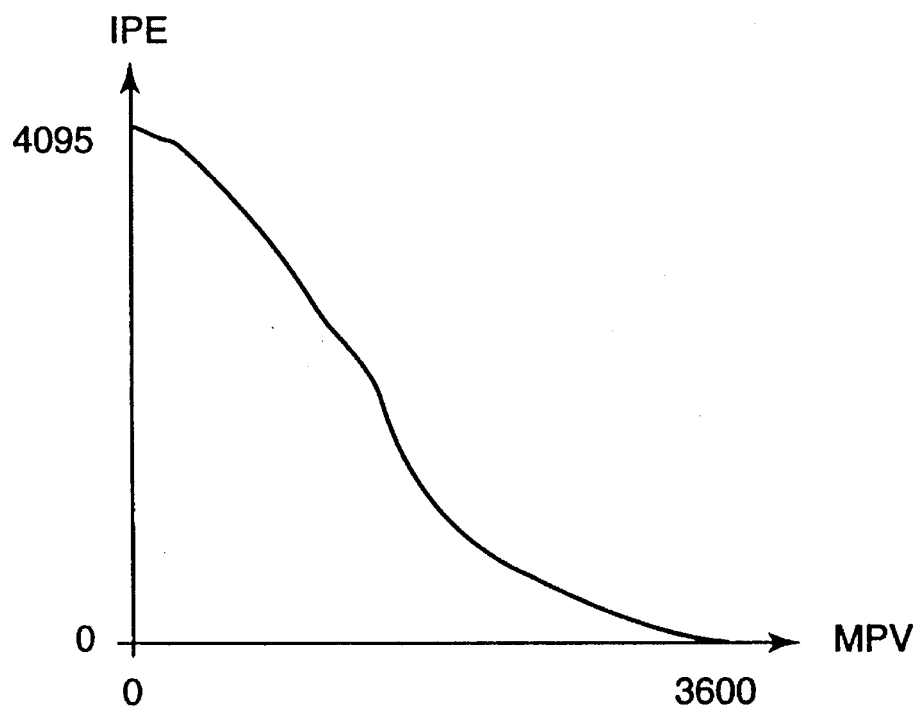
FIG. 11 is a graphical representation of the calibrated values for LUT C.

The general form for LUT C is depicted in FIG. 11 for the Film Digitizer as the input modality. Note that LUT C is primarily used to map the source pixel values to printed film density. In its most general form, LUT C also compensates for different film speed and contrast characteristics, reduced film density dynamic range and for film-processor-induced deviations from the desired transfer function.

Software Functional Description

The present invention includes software operating on a computer to measure the performance of all components of the electronic digital imaging system. The present invention monitors image quality throughout the system to measure a wide variety of potential image quality degradation sources. The use of an automated system to measure image quality throughout the electronic imaging system allows for a far greater accuracy in measuring system performance above and beyond traditional visual or interactive diagnostic procedures. By incorporating image quality metrics within the electronic imaging system, automatic assessment of the current level of image quality throughout the system is effected. A measurable level of image quality is obtained through the use of a set of consistent statistical image quality metrics automatically computed with very little operator assistance. The result of this software system is a completely objective, repeatable process that can be invoked by the users of this system at a much higher frequency than what a field engineer could provide during periodic visits to a customer site.

The image quality control software of the preferred embodiment of the present invention applies a set of comprehensive image quality metrics to both the image acquisition and image print functions (laser imager) of the electronic imaging system. Only a subset of these metrics are applied to the image displays since only luminance measurements are economically feasible using automatic data collection methods. Thus, such CRT geometric aberrations such as focusing, distortion, or spatial resolution cannot be measured. It is assumed that most CRT displays are sufficiently reliable that their quality as to geometric or spatial resolution will be stable between relatively infrequent visits by a field maintenance person.

The most critical location within the automated image quality control system of the electronic digital imaging system shown in FIGS. 4A and 4B is at the site of the image acquisition, such as at film digitizer 408, which corresponds to the digitizer 210 of image acquisition device 10 of FIG. 2. The most logical point of locating the quality control hardware and software functions is where the digitized images are first available in memory. The film digitizer station 210 of FIG. 2 is, of course, attached to a host computer 209. The host computer in the preferred embodiment of the present invention is a Unix-based workstation with floating point hardware support for image processing operations. Sufficient memory in computer 209 is required to maintain the sample images, 409 and 410, as well as temporary image processing buffers for processing image metrics. This software system also has components which execute on the image server 201 which is also a Unix-based workstation. In addition, a data collection remote procedure would be required on the image review station 422 to collect luminance data from the monitor under test 415 during luminance testing using photometer 414.

The software in the preferred embodiment to the present invention is developed in C/C++ and is intended for operation using the UNIX operating system which is platform independent (with the exception of the floating point hardware support). Those skilled in the art will readily recognize that since the source code of the preferred embodiment of the present invention is implemented in "C" code, this provides platform independence for use with other operating systems such as DOS, MacIntosh, etc.

Automated Image Quality Control Software Components

Figure 12:
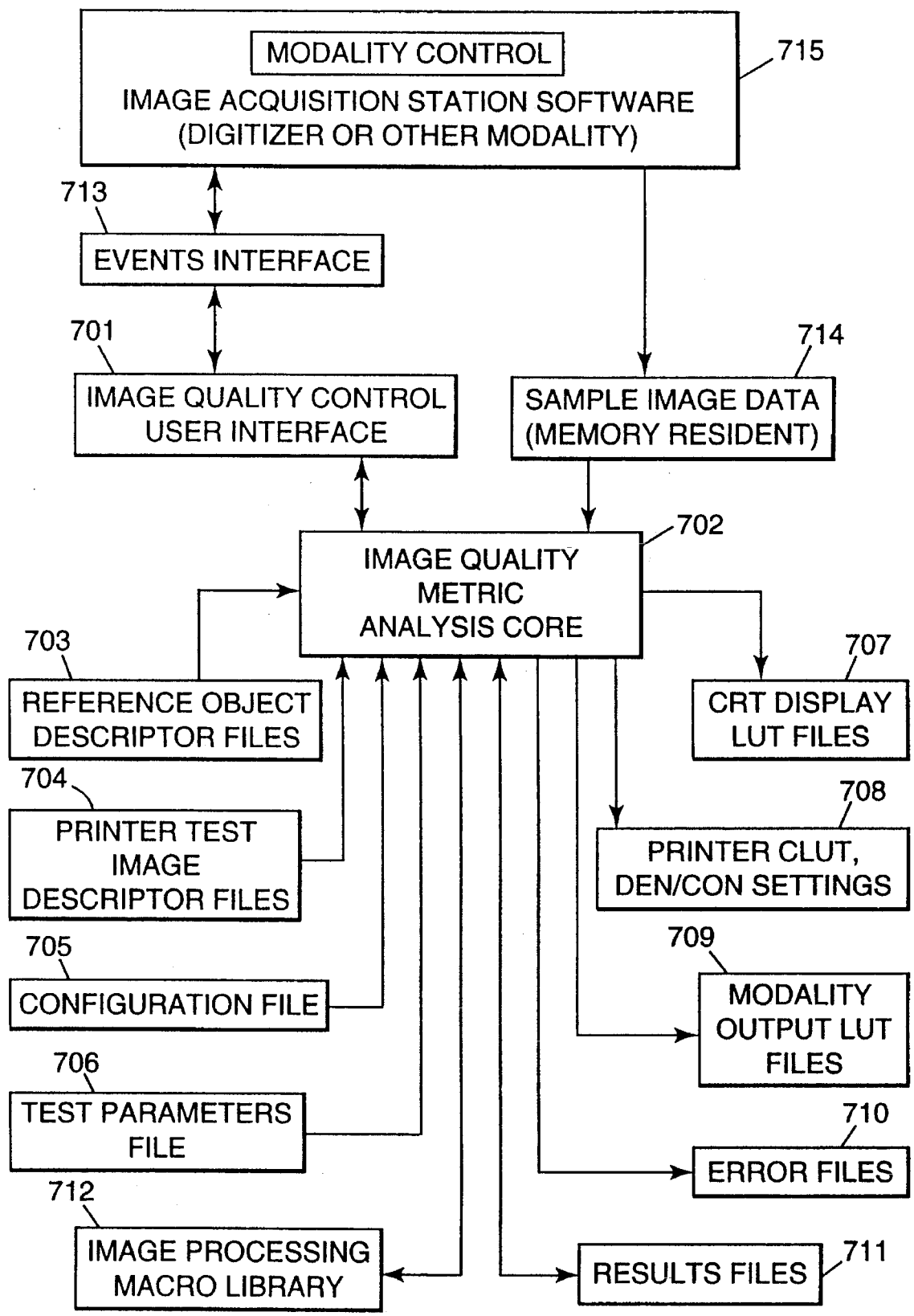
FIG. 12 is a block diagram of the automated image quality control software components of the preferred embodiment of the present invention.

FIG. 12 is a global flow diagram of the automated image quality control software components for the preferred embodiment of the present invention. The image quality control user interface 701 communicates with the user at a high level. This manager component of the software handles process control, parameter setting, user query, and notification of status. A database is maintained to save all results 711 from the automated quality control process managed by the image quality control user interface component 701 of the software 702.

The user has direct access to the automated image quality control software components through the image acquisition station software 715. The events/resource manager 713 is a lower level of resource manager used by the image acquisition station software 715 to control resources 703, 704, 705, 706, 707, 708, 709, 710 of the software system 702 at a lower level. Thus, information received from the film digitizer station software 715 which controls the input modality, such as an image digitizer, is under indirect control of the image quality control user interface 701.

The key component of the preferred embodiment of the present invention is the image quality metric analysis core software 702 which is written in C code and which contains the low level control to perform the variety of image quality metrics analysis required for system integrity and performance testing. Reference object descriptor file 703, printer test image descriptor file 704, configuration data file 705, and test parameters file 706 are inputs to this software analysis core 702 as constants to be used in measuring the actual values observed from the electronic digital imaging system.

The results of the image quality metric analysis are a variety of output files such as the CRT display LUT (Look Up Table) file 707, the primer CLUT (Contrast Look Up Table) file 708, the modality output, such as a digitizer, LUT file 709 and the error file 710. The results of these metric analysis are stored in an image analysis results database 711 for later use and review by qualified field personnel in locating and identifying the sources of degradation in the system.

The image quality metric analysis core 702 also relies on some third party image processing macro libraries 712 such as DIP Station or IP Lab Spectrum which are well-known to those skilled in the art. As described above in conjunction with Table 1, a wide variety of image quality metrics can be performed by the preferred embodiment of the present invention to analyze features and statistical quantifiers as to the performance of the system. Each of the metric analysis software routines used in the preferred embodiment of the present invention are described below.

Automated Image Quality Control Process States

Figure 13:
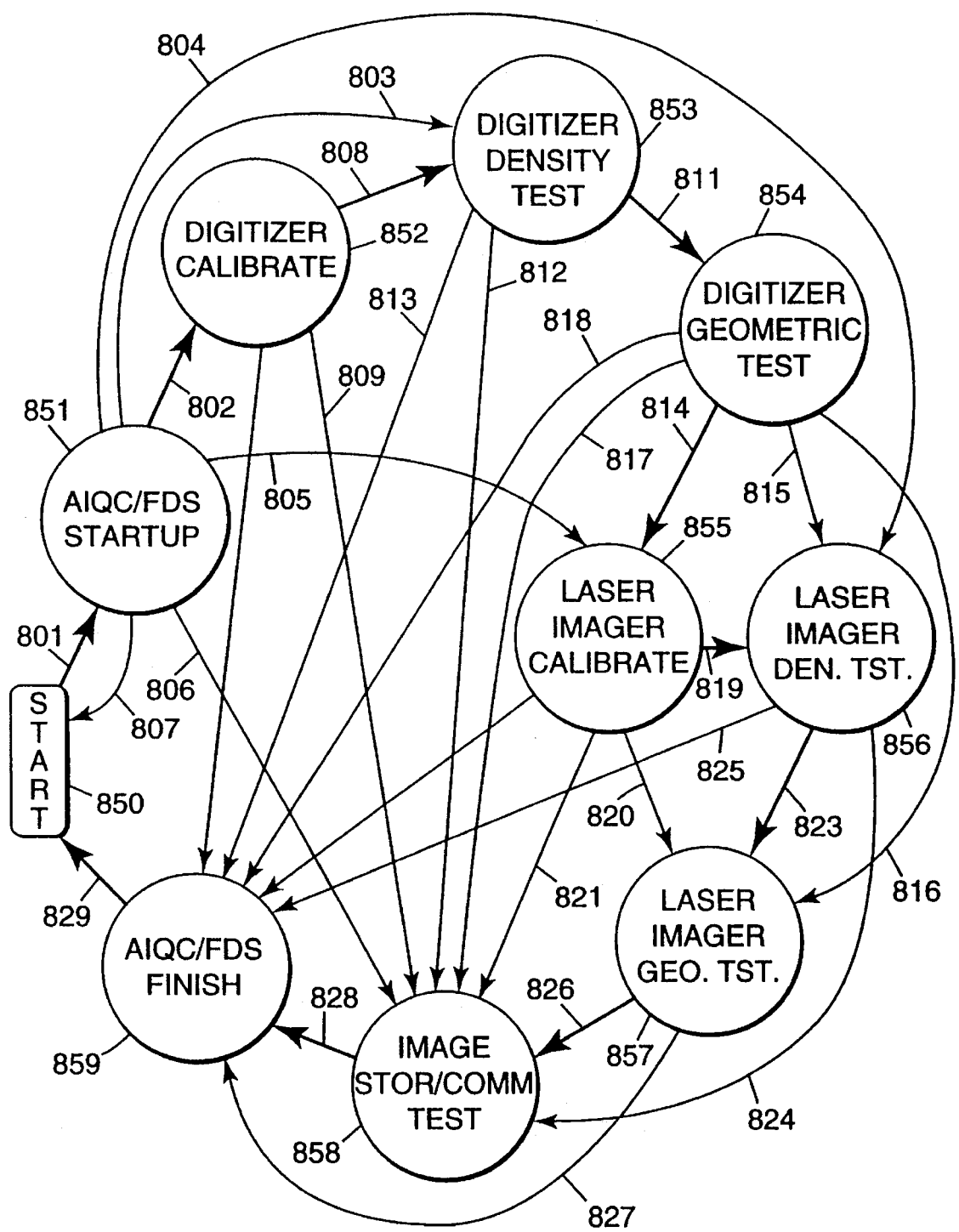
FIG. 13 is a state diagram of the procedures of the automated image quality control process of the preferred embodiment of the present invention.

FIG. 13 is a state diagram showing the automated image quality control process of the preferred embodiment of the present invention. This quality control process begins with the user of the system making a quality control menu selection at the image quality control user interface 701 of FIG. 12. A quality control menu selection is made which brings up a screen which informs the user about the proposed sequence of test or calibration defined by the configuration file. The only option would be to continue or, had the selection been made erroneously or work flow demands, it could be cancelled. The complete set of procedures that may be executed by an operator include film digitizer calibration 852, film digitizer densitometry test 853, film digitizer geometric test 854, laser imager calibration 855, laser imager densitometry test 856, laser imager geometric test 857, and image storage and communication test 858. The execution sequence of these procedures is controlled by a variety of factors described more fully below.

The CRT calibration and test procedure is ordinarily performed by a field service engineer using a photometer to complete the test. This test is described below in conjunction with FIG. 22.

FIG. 13 shows the complete set of automated image quality control procedures for execution on the film digitizer station 209. Those skilled in the art will readily recognize that a computed radiography interface for the electronic imaging system of the preferred embodiment of the present invention would require a similar process state diagram for testing the quality of that image acquisition device. FIG. 13 shows state transition paths which may occur between the various steps of the complete set of procedures. The bold lines 801, 802, 808, 811, 814, 819, 823, 826, 828, and 829 of the process state diagram of FIG. 13 show the successful result paths between the various states of the procedure for a system operating within acceptable limits. The remaining paths of the state diagram are taken in the event that errors occur in the process (such as invalid calibration results) or image quality metrics have exceeded the "fatal" level thresholds, thereby terminating the process.

FIG. 13 also defines a philosophy of result reporting wherein each procedure stores its own results in the log files and additionally generates warning or fatal level error messages in an error file as they are encountered. The approach shown generates only one type of error message (warning or fatal) for each metric type. A warning level exceedance of a metric is not considered a negative result except that it could be used by higher level software to generate an automatic service notification that a problem may occur in the near future for this component in a particular category (predictive servicing). Normal users of the automated image quality control application would never see a warning level notification. Rather, this category of error would appear on a system administrator console for informational purposes only. For each test comparison, the return status is updated appropriately.

At the conclusion of each procedure, messages are displayed on the film digitizer station screen indicating the interpreted result status (warnings are concealed as successful results). At this time, results are also saved. Other results are saved for performance tracking and as an aid to troubleshooting component failures. After the completion of each procedure, the user's screen indicates the next procedure to be executed and control then passes to that procedure.

Beginning at the start state 850, control is passed 801 to the startup routine 851. The startup routine notifies the user as to which test is to be performed based upon prestored test configuration information (which can be changed as necessary). Usually, the digitizer calibration test 852 is selected first. The user has the option, however, of directly selecting the digitizer density test 853, the laser imager density test 856, or the laser imager calibration 855.

Usual control is passed 802 to the digitizer calibration procedure 852. Normal completion of the digitizer calibration passes control 808 to the digitizer density test 853. A failure of this test will pass control either to the image storage and communication test 858, or to the completion of the test 859 upon a fatal error.

The digitizer density test 853 is next performed. Again, a failure of this test passes control either to the image storage and communication test in the case of a warning message, or to the completion routine upon fatal termination of this test.

With a normal completion of the digitizer density test 853, control is passed 811 to the digitizer geometric test 854. Again, a warning message terminating this test would pass control to the image storage and communication test 858 or, in the case of a fatal termination, control is passed 818 to the completion routine 859. Under certain conditions, the digitizer geometric test 854 will skip the laser imager calibration test 855 and pass control to the laser imager densitometry test 856, or to the laser imager geometric test 816 if the user so selects to ignore the laser imager calibration test 855.

Normal flow of the battery of tests would pass control from the digitizer geometric test 854 to the laser imager calibration procedure 855. This is the recommended path, since calibrating the laser imager is an important prelude to the laser imager densitometry test procedure 856 and the laser imager geometric test procedure 857. Again, a warning level termination of the laser imager calibration procedure 855 sends control to the image storage and communication test procedure 858. A fatal termination of the laser imager calibration procedure 855 passes control to the completion procedure 859. Normal termination of the laser imager calibration procedure 855 passes control to the laser imager densitometry test 856.

The laser imager densitometry test procedure 856 could terminate with a warning message sending control to the image storage and communication test procedure 858. A fatal termination of the laser imager densitometry test procedure 856 sends control to the completion procedure 859. Normal completion of the laser imager densitometry test procedure 856 passes control to the laser imager geometric test procedure 857.

The laser imager geometric test procedure 857 could terminate the test with a fatal error, sending control directly to the completion procedure 859. Normal completion of the laser imager geometric test procedure 857 passes control to the image storage and communication test procedure 858. In all cases, termination of the image storage and communication test procedure passes control to the completion procedure 859, which finally terminates the process back at the start procedure 850.

Detailed Description of Flowcharts

From the user's perspective an initial screen is presented which contains a listing of the proposed execution path for the test procedures shown in the state diagram of FIG. 13. The list will be based upon an initial evaluation of the configuration and status variables without regard to the result variables. The purpose of this list is to remind the user of the sequencing of the tests. The user is given a choice to either continue or to cancel the automated image quality control process altogether. If the 'continue' option were chosen, the startup procedure passes control to one of the five next procedures described above. Each of the procedures described in FIG. 13 are described more fully below in the form of flowcharts.

Automated Image Quality Process Control Flow

Figure 14A:
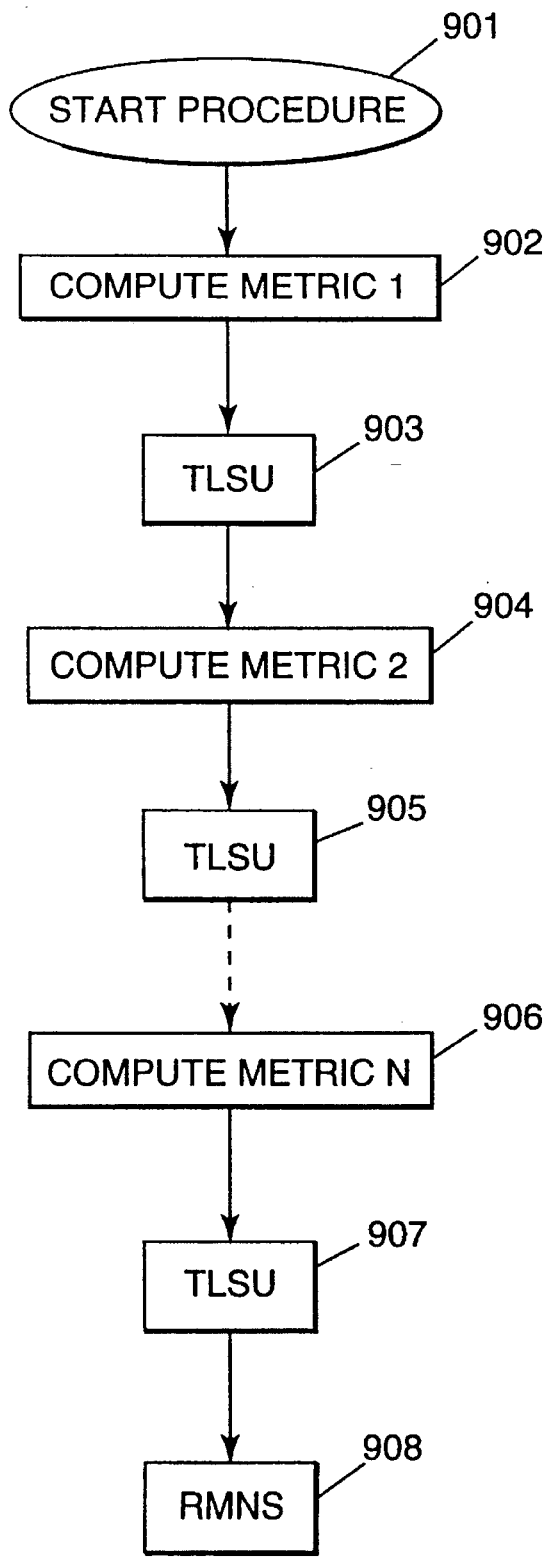
FIG. 14A is a flow chart showing the computation of metrics and message reporting for each procedure of FIG. 13 for the automated quality control process of the preferred embodiment of the present invention.

FIG. 14A is a process flowchart for any of the procedures 852, 853, 854, 855, 856, and 857 of FIG. 13. Each of the procedures of FIG. 13 compute a number of metrics as shown in FIG. 14A. Thus, each procedure of FIG. 13 computes a plurality of metrics as described above in conjunction with Table 1.

Figure 14B:
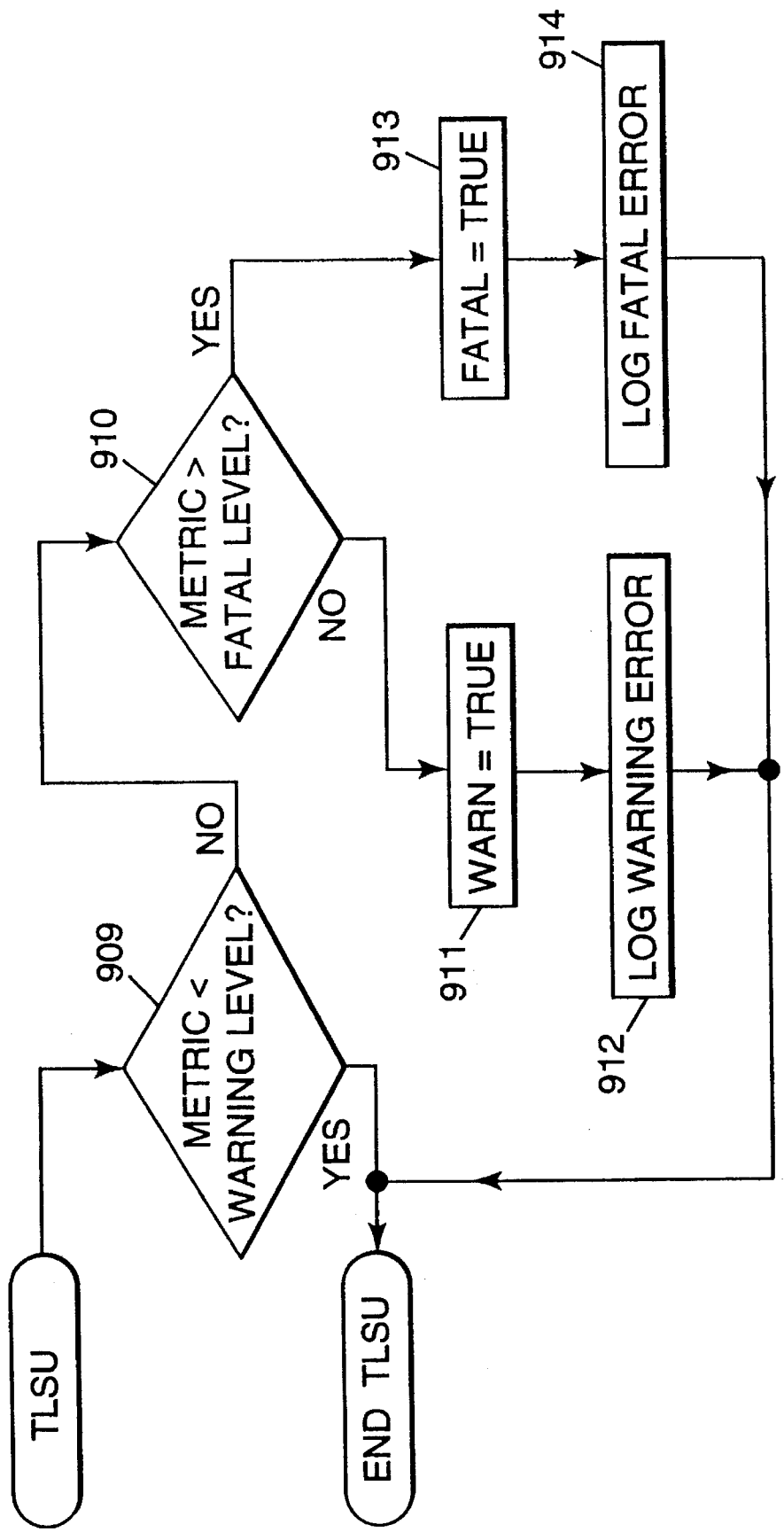
FIG. 14B is a flow chart showing the test, log, and status update (TLSU) reporting procedure of FIG. 14A.

Each procedure may compute a different number of metrics as shown as metric 1 through n in FIG. 14A. After the computation of each metric 902, 904, and 906, a metric Test, Log, and Status Update (TLSU) process 903, 905, and 906 is performed, which is shown in more detail in FIG. 14B. For example, after the first metric is computed 902, TLSU process 903 is executed. The TLSU process performed after each computation of each metric determines which type of message is to be reported in the log file. As shown in FIG. 14B, if the metric calculation exceeds a first threshold level 909 but not a second threshold level 910, a warning message is generated 911 and placed in the message log 912. If a second threshold 910 is exceeded for the computed metric, the TLSU routine 903 will put a fatal error message 913 in the log 914. Thus, the log is updated with each of the computed metrics and the results of the metric calculation compared against threshold levels.

Figure 14C:
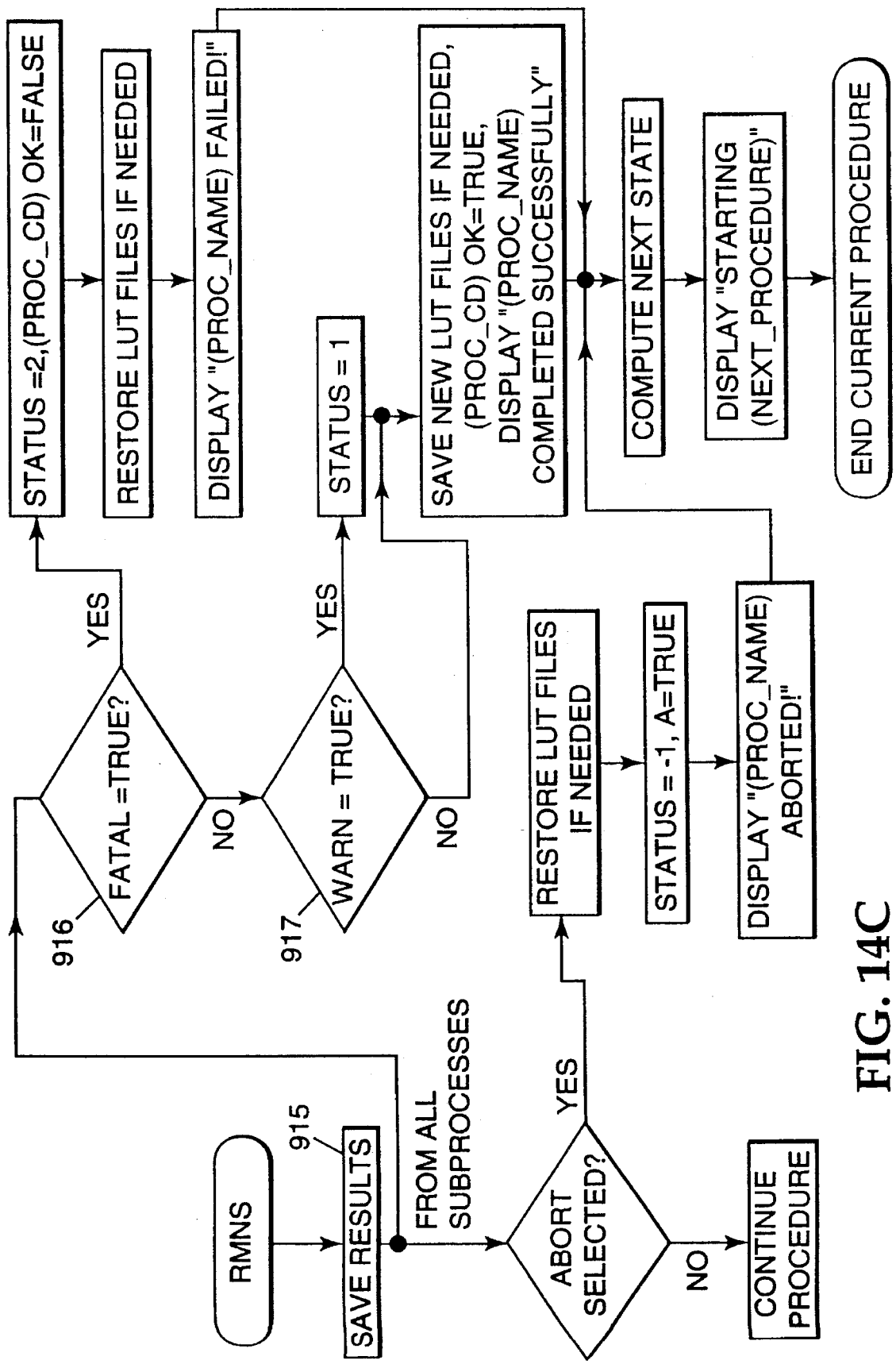
FIG. 14C is a flow chart showing the result, messaging and next state processing (RMNS) procedure of FIG. 14A.

After the completion of all metrics, and the completion of all TLSU procedures, a result messaging and next state processing (RMNS) routine 908 is executed to determine which state in FIG. 13 is to be executed next. The result messaging and next state processing (RMNS) routine 908 is shown in FIG. 14C. If, for example, a fatal error is encountered in any of the computed metrics, the RMNS routine will return control to the finish or completion procedure 859 shown in FIG. 13. If a warning message is computed, the next state in FIG. 13 is computed and control is passed to that routine.

Film Digitizer Calibration

Figure 15:
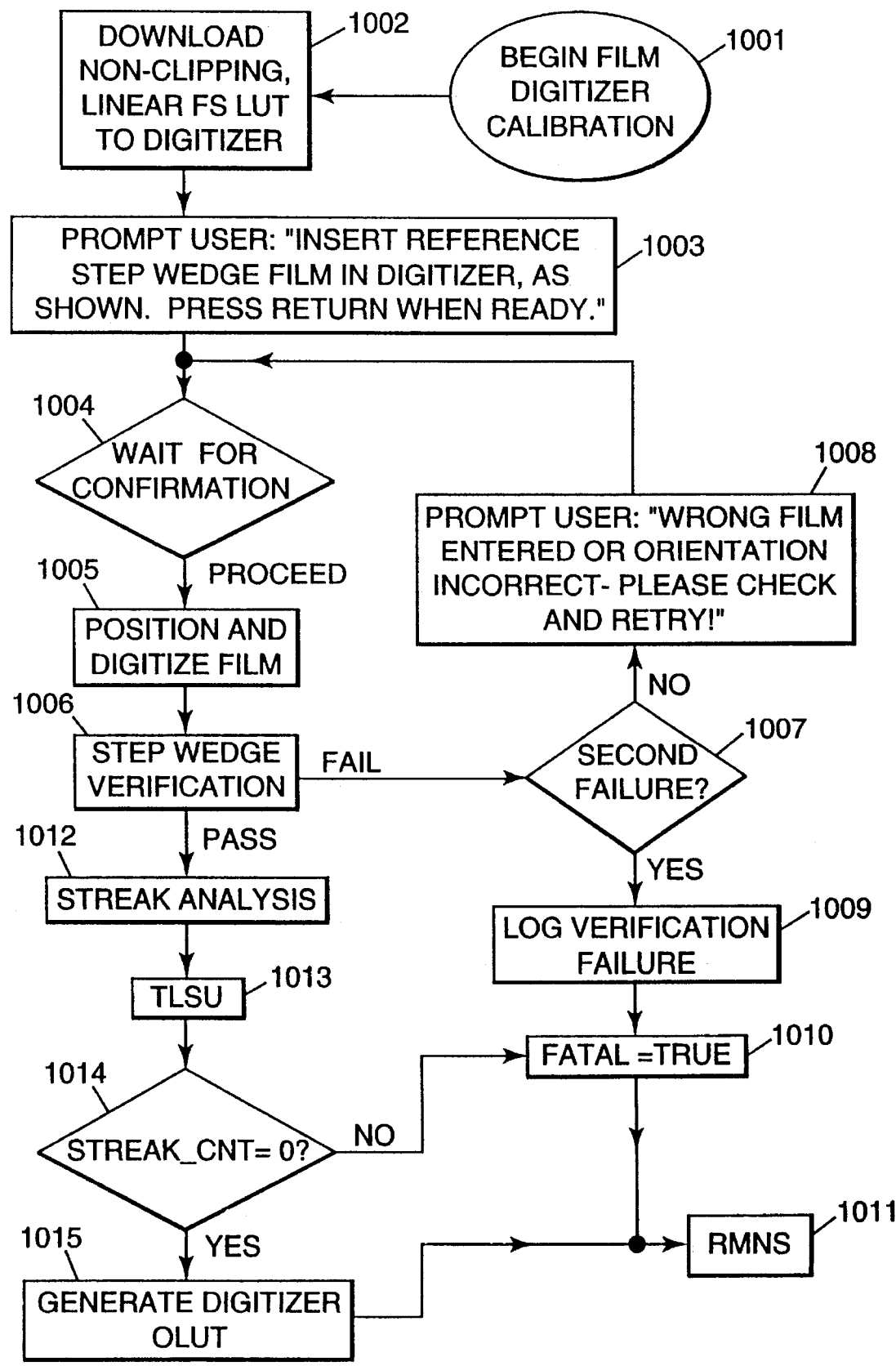
FIG. 15 is a flow chart for the film digitizer calibration procedure of FIG. 13.

FIG. 15 is a flowchart for the film digitizer calibration procedure of FIG. 13. The purpose of the digitizer calibration is to ensure that the measured density error is kept to within a predetermined tolerance. The approach taken is to use the referenced step wedge film in conjunction with a linear full scale digitizer output LUT to obtain the raw digitizer transfer function. From this, a new LUT is computed which, when loaded into the digitizer, should produce the expected linear transfer function between actual and measured density. For the Lumisys digitizer, this corresponds to pixel values having a least significant bit of 0.001 optical density and a hard limit for inputs of greater than 3.6 optical density.

This process is shown in detail in FIG. 15. First, a prestored linear full scale output LUT (i.e., without the usual clipping function at 3.6 over 3600) is downloaded to the digitizer 1002. Then the system prompts the user to insert the step wedge film correctly at 1003. Upon continuation that the film has been entered 1004, it is digitized at 1005. After film digitization at 1005, the step wedge digital sample image is next checked at 1006 to verify that it is both the correct film and in the correct orientation. A failure sends control to 1007. The user is given a second chance to correct the situation at 1007. If it is not second failure, the user is given a message at 1008 and the process starts anew at 1004. If the second failure of the correct orientation or correct film is indicated, the failure is logged at 1009, a fatal flag is set at 1010, and the result massaging and next state processing routine at 1011 is invoked to complete this procedure.

Assuming the correct orientation and correct film has been entered and digitized, the digital sample image is checked for the presence of streaks at 1012. This is necessary to ascertain that both the digitizer optics are clean, and that no significant scratches have been introduced into the referenced film. Control is then passed to the metric test log and status update routine 1013, and the number of streaks are counted at 1014. If any streaks are found, a fatal error message is logged at 1010 and the procedure completes at the RMNS routine 1011. If no streaks are found, control is passed to 1015, where the system generates a new, but not necessarily linear, output LUT. If there were no errors in this calibration routine of FIG. 15, a new OLUT (Output Look Up Table) is both stored for later use and downloaded to the digitizer.

If an error had occurred or, if abort were selected by the user, then the error condition would be logged and the most recent digitizer output LUT would be restored in the digitizer. The next procedure to execute would depend on the state of the results of this test as shown in the state diagram of FIG. 13. Note that in this procedure, and in the laser imager calibration procedure described below in conjunction with FIGS. 18A and 18B, there is no single metric computed from which to assess the efficacy of the result. These are merely calibration algorithms.

Film Digitizer Density Test Procedure

Figure 16A:
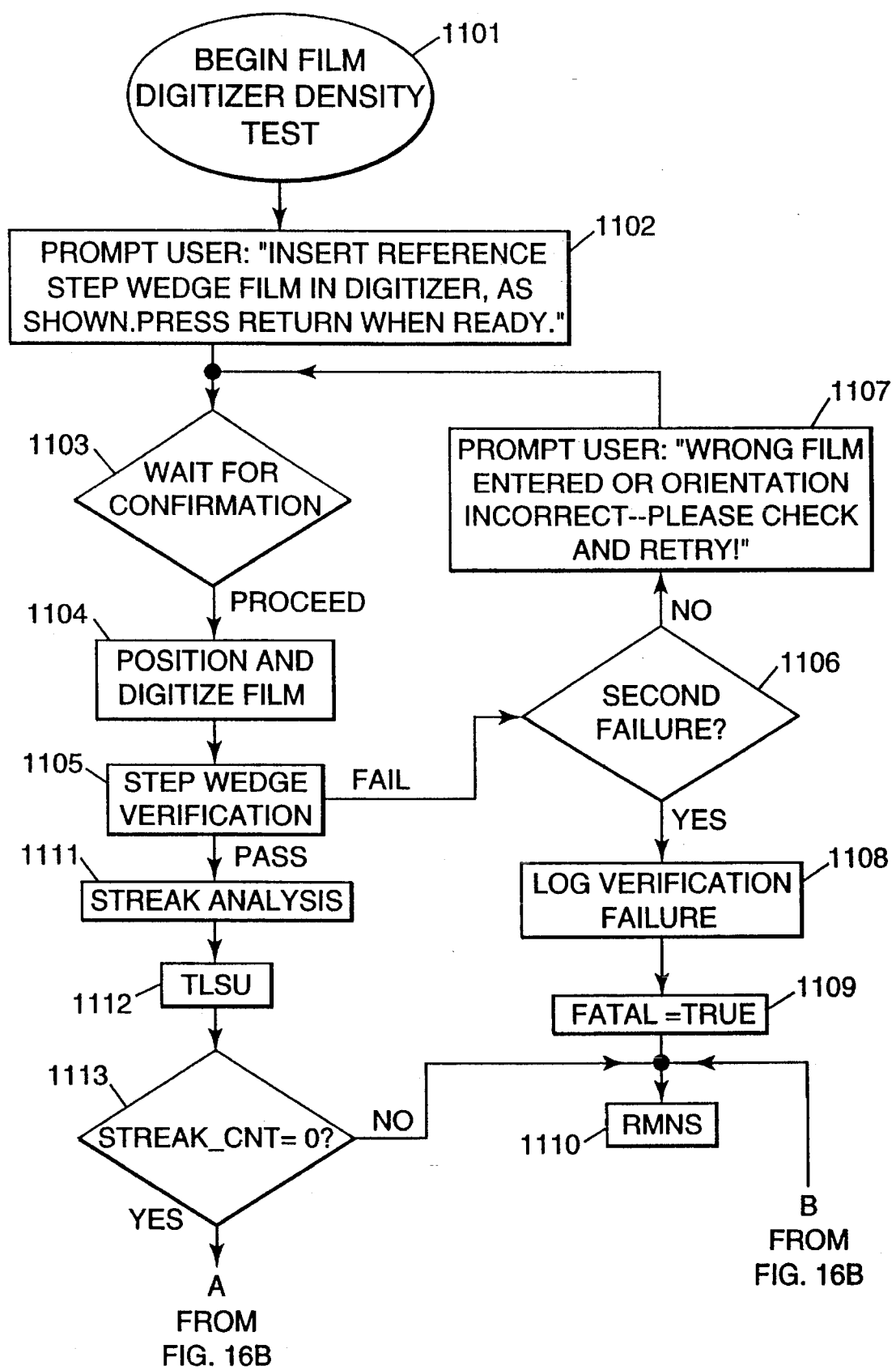
FIGS. 16A and 16B are flow charts for the film digitizer density test procedure of FIG. 13.
Figure 16B:
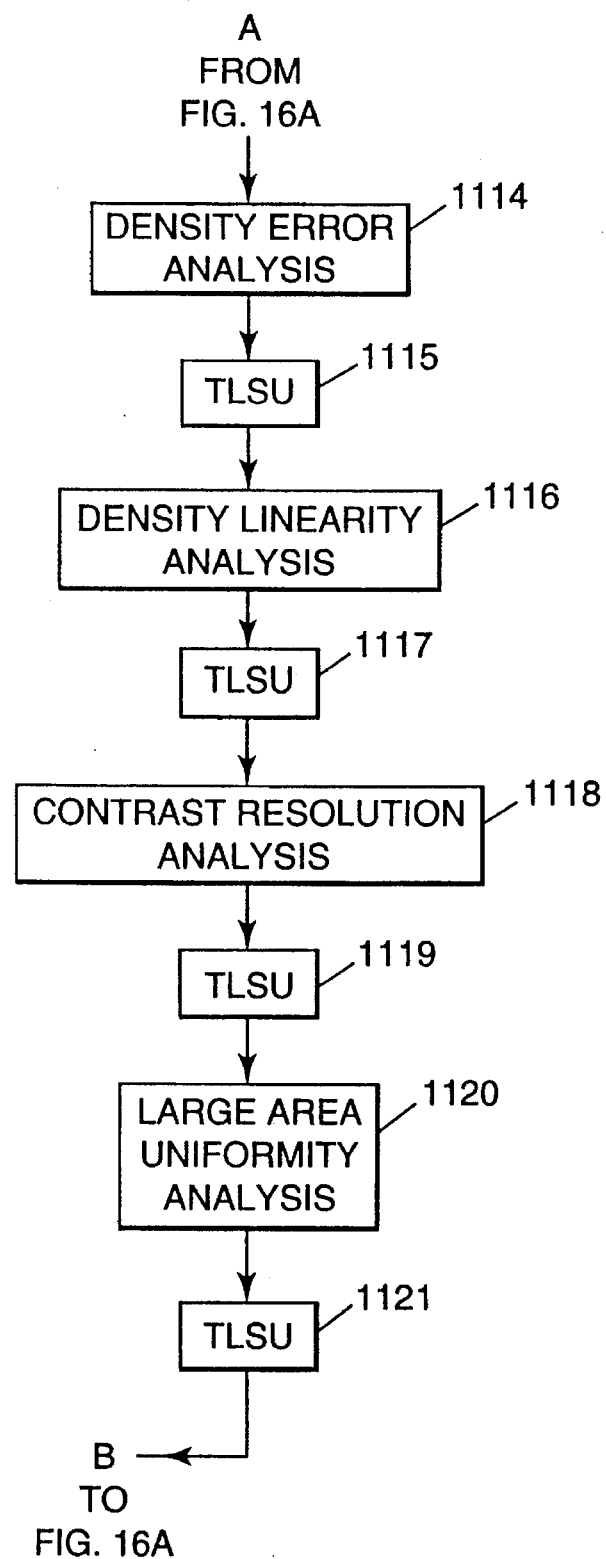

FIGS. 16A and 16B describe the film digitizer density test procedure. The densitometry test of the film digitizer is ordinarily exercised following a successful calibration procedure. In this case, the system is verifying that the just-computed output LUT produces the desired result. This procedure can be invoked by skipping the digitizer calibration and using the existing LUT.

In beginning the film digitizer density test at 1101, the user is prompted to insert or possibly reinsert the referenced step wedge film at 1102. After the usual digitization and verification cycle, the streak check is performed at 1111, as was done for the digitizer calibration. Again, if no streaks were detected, a series of four tests are conducted: absolute density error 1114, best fit density linearity 1116, contrast resolution analysis 1118, and large area uniformity analysis 1120.

Film Digitizer Geometric Test Procedure Flow

Figure 17A:
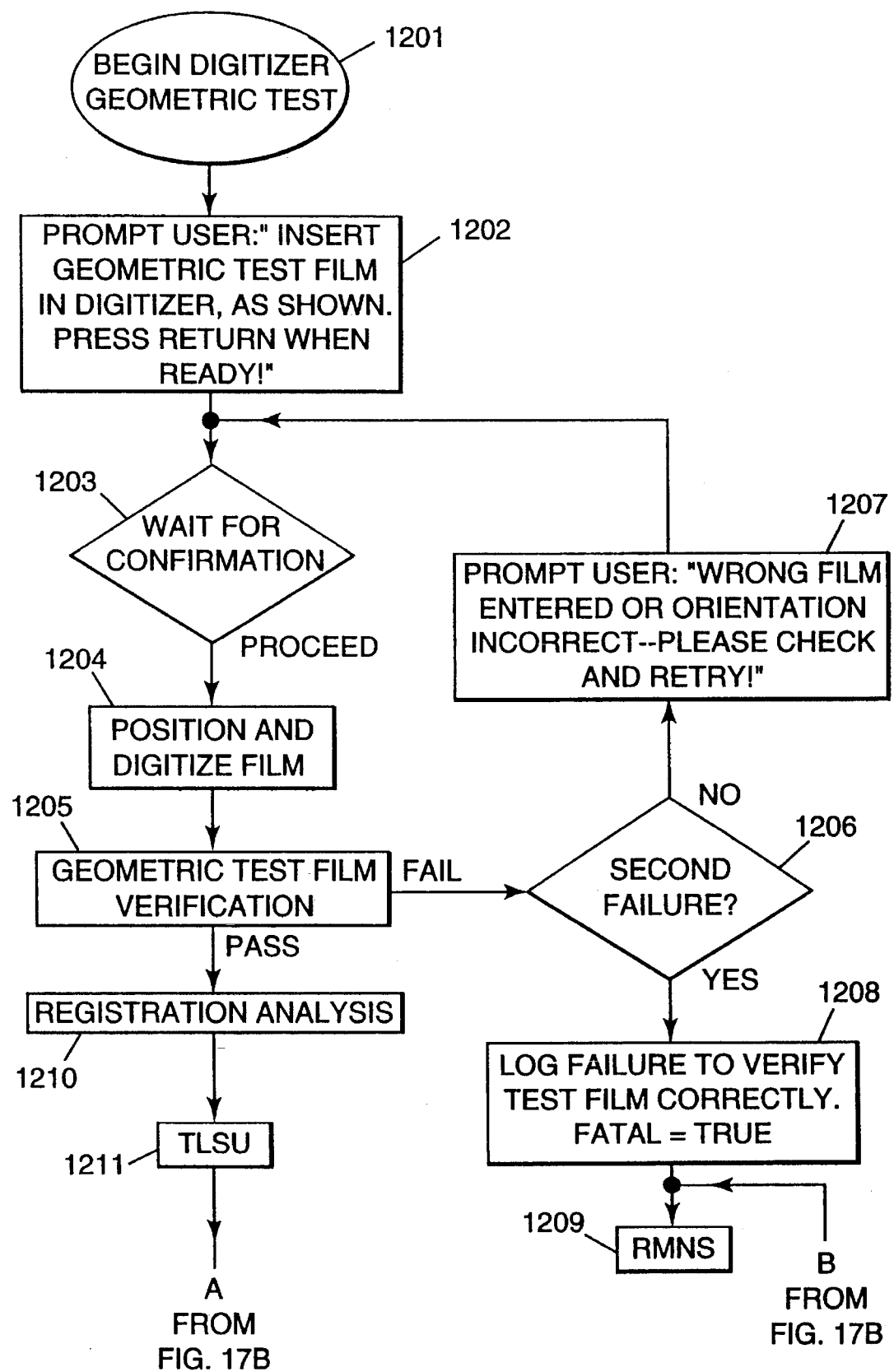
FIGS. 17A and 17B are flow charts for the film digitizer geometric test procedure o f FIG. 13.
Figure 17B:
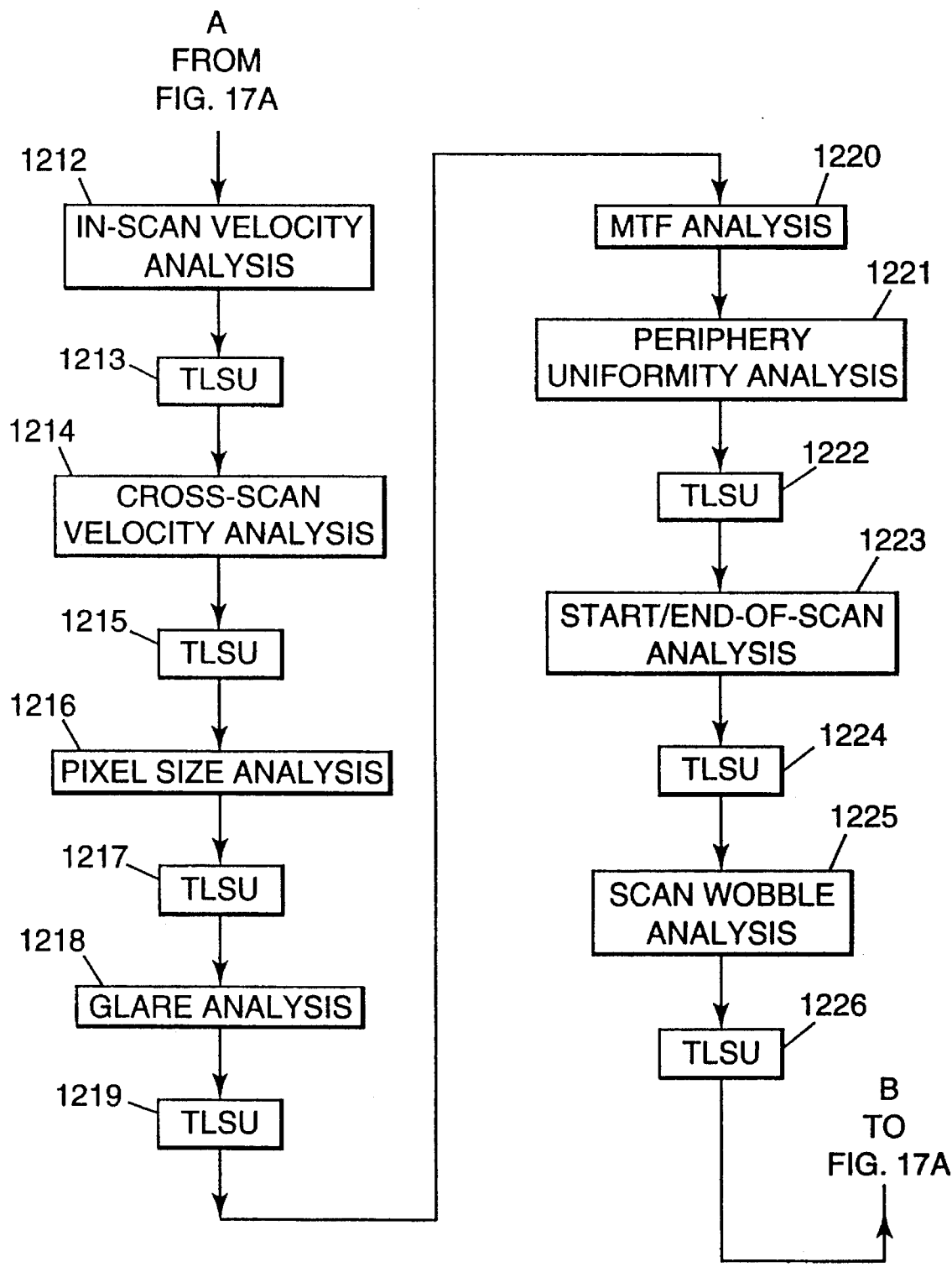

FIGS. 17A and 17B describe the process for the film digitizer geometric test. If the geometric tests are enabled by the user, then this procedure will begin flow at 1201 as shown in FIG. 17A. To reach this procedure requires that the digitizer density test procedure has been executed successfully as shown in FIGS. 16A and 16B. As is common in these routines, the user is prompted to insert the geometric test film 404 in the digitizer at step 1202. A similar process of verification with one retry is allowed as described above in conjunction with FIG. 15.

The geometric tests begin with a step to register the image obtained by digitization 1210. Became many of the tests to be performed involve the placement of small regions of interest in precise locations as shown on the geometric/MTF reference image of FIG. 5, the system needs to know if there are any x or y translations of the image as it was digitized. From the registration analysis using the registration target 508 of FIG. 5, an offset is determined that is used by all subsequent tests.

After registration, a sequence of eight image feature extractions and performance metrics are computed as shown in FIG. 17B. These eight areas are: in-scan velocity uniformity analysis 1212, cross-scan velocity uniformity analysis 1214, pixel size and aspect ratio analysis 1216, normalized glare area analysis 1218, horizontal and vertical MTF and a number of frequencies at 1220, periphery uniformity analysis 1221, start and end of scan position uniformity (jitter) analysis 1223, and scan wobble (laser beam wobble) analysis 1225. While the analysis will find the MTF at a number of frequencies, in practice, the system will likely only test the MTF value at a single frequency as the performance metric. In the preferred embodiment of the present invention, the value at or near 1.0 lp/mm will be tested.

Laser Imager Calibration Procedure Flow

Figure 18A:
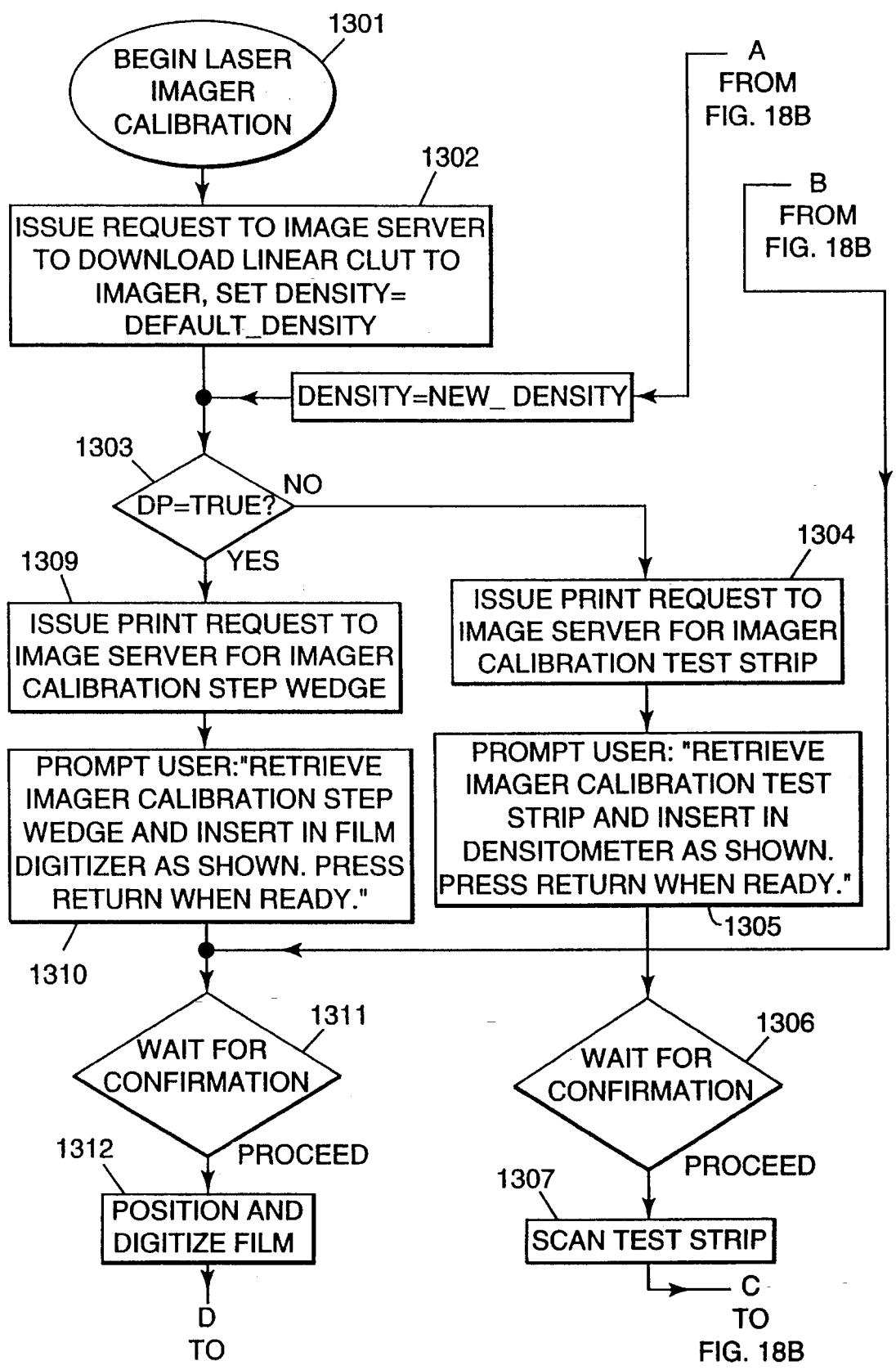
FIGS. 18A and 18B are flow charts for the laser imager calibration procedure of FIG. 13.
Figure 18B:
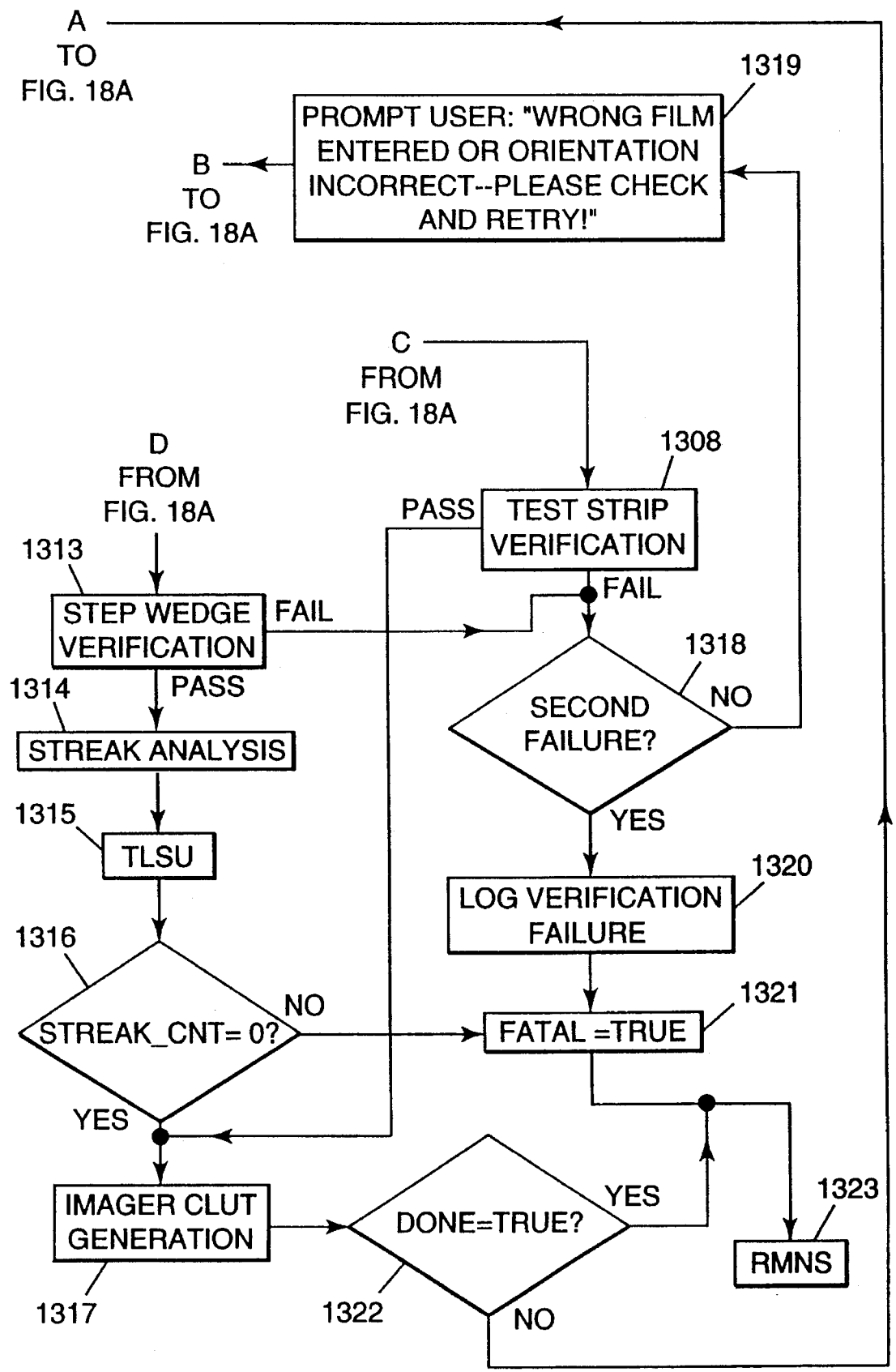

FIG. 18A and 18B are flowcharts showing a laser imager calibration procedure. In the preferred embodiment of the present invention, the laser imager is selected to be Model No. 959 or 969 laser imagers available from Minnesota Mining and Manufacturing Company, the assignee of the present invention. The Model 969 imagers incorporate a closed-loop density and contrast control mechanism internally. This feature eliminates the need for periodic calibration for the sake of densitometric reproduction accuracy. However, the earlier Model 959 machines are "open-loop" and are susceptible to considerable density and contrast changes as a result of chemistry, film and laser power variations. Thus, depending on the type of laser imager used in an electronic imaging system, the automated image quality control functionality of the preferred embodiment of the present invention is essential for calibrating and maintaining proper operability of laser imagers due to the excessive variability within and between different laser imagers.

The feedback device for obtaining printed film densities from a sample film is the film digitizer 408 of FIG. 4B. However, some systems may not have a film digitizer 408 as the primary input modality. For example, a computed radiography input modality may be substituted for the digitizer. In this instance, a self-scanning spot-type densitometer will be incorporated in the system as a means for densitometry feedback.

The imager calibration process is shown in FIG. 18A and 18B. First, a nominal density setting and a linear CLUT are downloaded to the imager to be calibrated at 1302. Then, a print request is issued at 1303. The sample film to be printed will depend upon whether or not there is a digitizer present in the system of FIG. 4A and 4B. If there is, a step wedge will be printed at 1309. Otherwise, a sheet of film with an embedded test pattern suitable for reading by the densitometer will be made. The user is prompted to process or retrieve the resulting sample film at 1310 and place it in the appropriate reading device. If a step wedge has been made at 1309, then it is digitized and verified for correct orientation at 1312 and 1313, just as in the digitizer calibration and test procedure described above in conjunction with FIG. 15.

After the film is verified, a streak analysis is performed at 1314. If the system is using the densitometer at 1304, an orientation test would be performed at 1308. However, the streak testing and analysis at 13 14 would be skipped, since it cannot be done with a spot reading device.

Next, the new CLUT for the imager is generated at 1317. This process will examine the printed film $D_{max}$ (maximum density obtained) and decide if any density adjustment needs to be made. At this time, a check is made to see if the desired density can be obtained at all, or if a compromise must be made. If it is found that the density change can be made, the CLUT generation process will terminate without setting its DONE flag to be true at 1322. It will also output the new density to be used. At this point, a new sample film would be produced and the process would be repeated.

The CLUT generation algorithm will signal completion by setting DONE to be true. At this time, it will also set the appropriate warning or fatal error flags indicating the type of calibration result achieved. A warning in this case would be interpreted to mean that the imager calibration was successful only after a compromise to the desired $D_{max}$ had been made. A fatal error occurs when it is found that not even a compromised $D_{max}$ could be obtained.

Finally, the new CLUT is saved to the default LUT file at the image server for future print requests. It is also saved as a named result file for later reversion in case of future errors. Other results obtained during the calibration process are also saved at the RMNS routine 1323. The next step in the process is then determined by the RMNS routine to move control flow as shown in FIG. 13 from the laser imager calibration procedure 855 on to the next step.

Laser Imager Density Test Procedure Flow

Figure 19A:
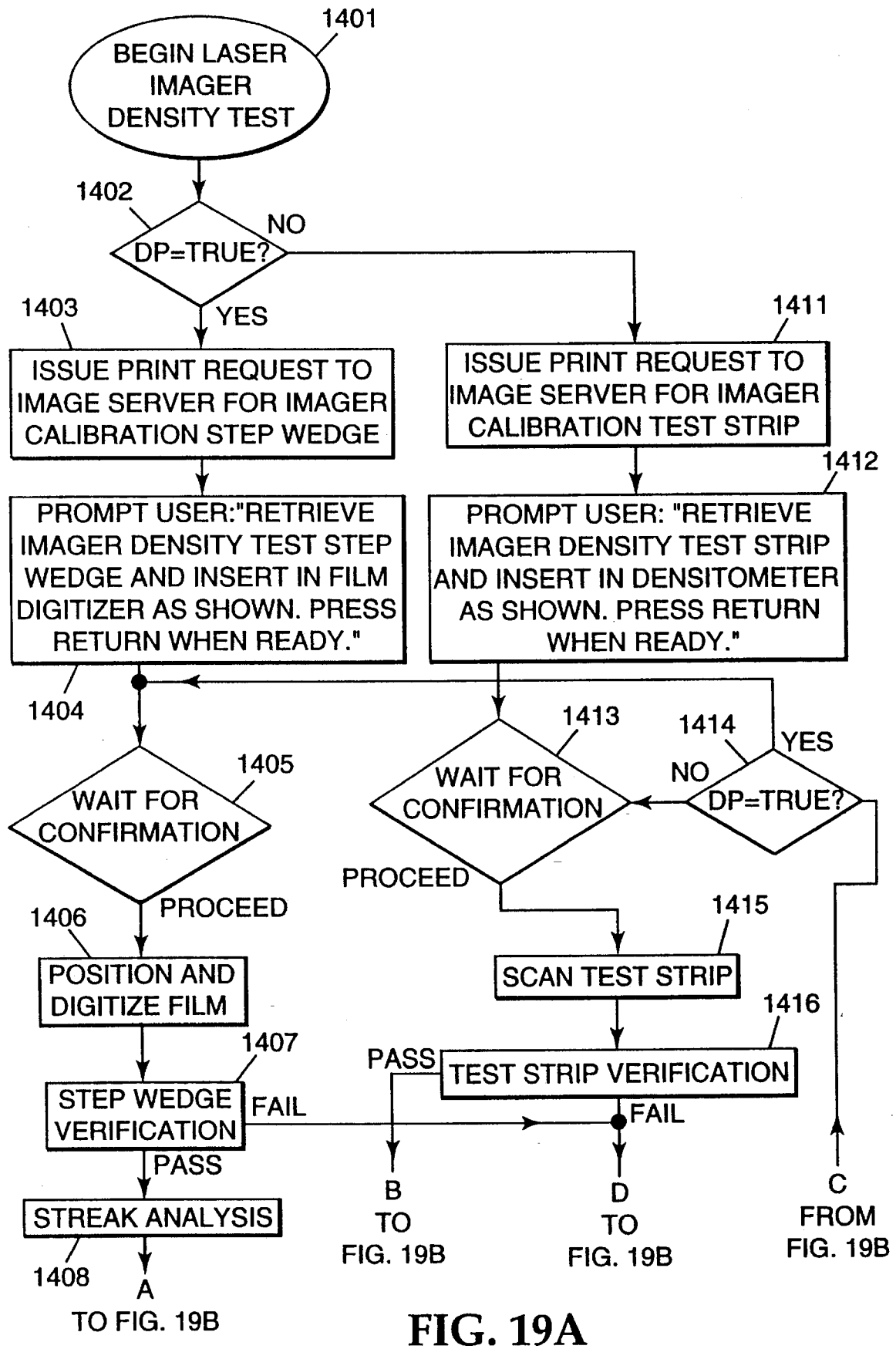
FIGS. 19A and 19B are flow charts for the laser imager density test procedure of FIG. 13.
Figure 19B:
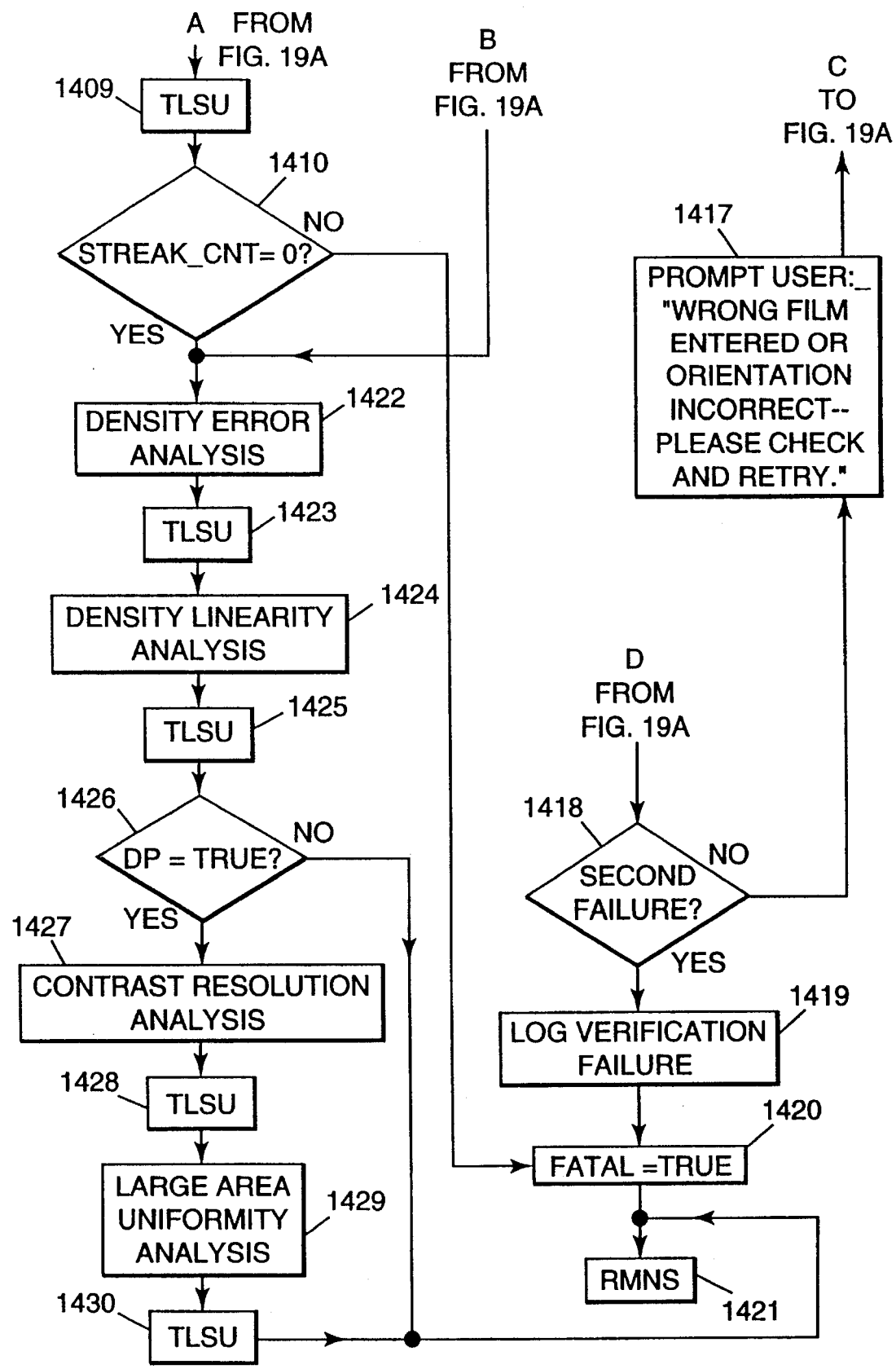

FIGS. 19A and 19B describe the laser imager density test procedure flow. The laser imager density test may be either as a postcalibration verification of the just computed CLUT or it may be entered into directly from the digitizer testing sequence as shown in FIG. 13. In either event, this procedure of FIG. 19A and 19B begins exactly like the laser imager calibration as shown in FIG. 18A. After the process of printing the appropriate sample film, scanning and digitization and verification, the actual densitometry testing begins in FIG. 19B. The only difference between the testing in FIG. 19B and the testing done in the digitizer densitometry tests of FIGS. 18A and 18B is that a different set of descriptor files and test thresholds are used. The descriptor files for the imager tests account for the minification of the images that occurs on printing, as well as a modification of the expected density characteristics in the laser imaged films. The test results file will be different to account for the fact that the sample images, once digitized, will contain degradations due to both the imager and the digitizer. Thus, the thresholds used to test the results will be relaxed enough to account for the cascade effect incurred. Note also that if a densitometer were being used to obtain the data, that the last two processes of uniformity 429 and contrast resolution testing 427 would be skipped.

Laser Imager Geometric Test Procedure

Figure 20A:
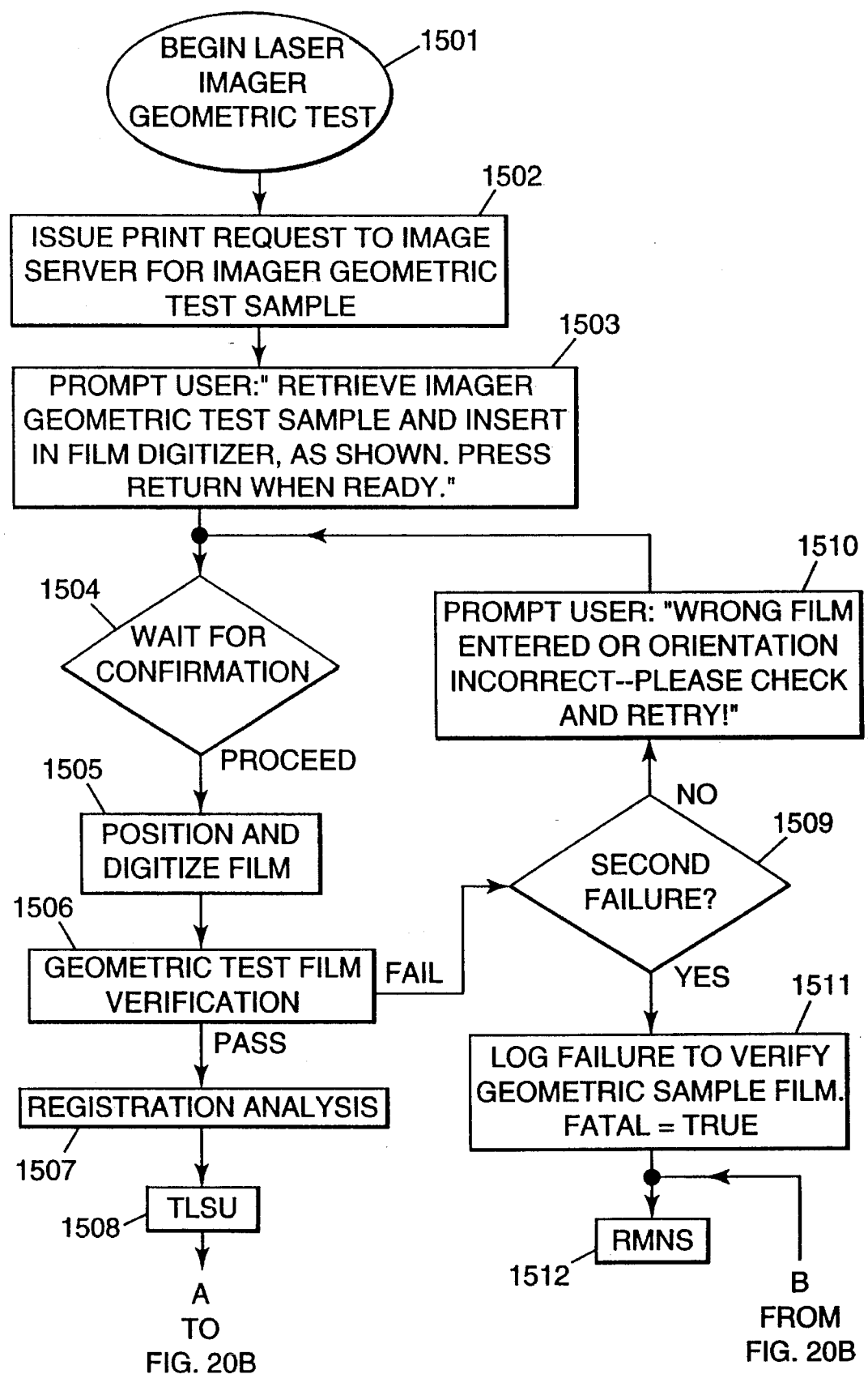
FIGS. 20A and 20B are flow charts for the laser imager geometric test procedure of FIG. 13.
Figure 20B:
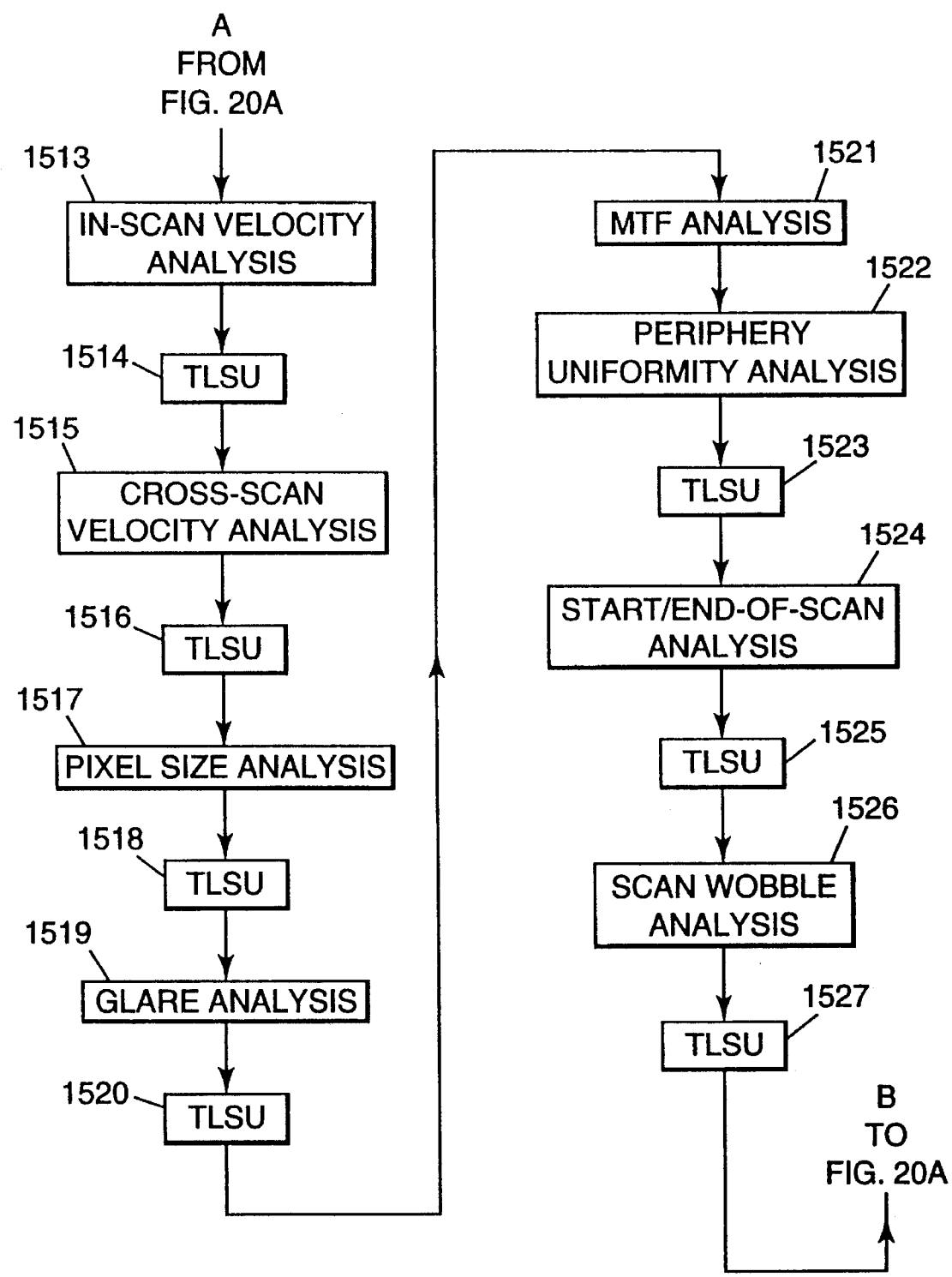

FIGS. 20A and 20B describe the laser imager geometric test procedure flow. This procedure, when enabled, can only be performed in conjunction with a film digitizer, and will proceed in the same manna as for the digitizer geometric test procedure with the exception that a different descriptor file for the geometric sample film will be referenced. Also, the test thresholds for the various MTF and geometric metrics will differ from the digitizer case because of cascaded degradations, differences in film color, and generally different performance behavior between the laser imager and the film digitizer.

Image Storage and Communications Test Procedure Flow

As described above, another form of image quality degradation is due to faults in the communication and storage paths as image data moves through the system. In the preferred embodiment of the present invention, image communication errors may occur between the digitizer, and the film digitizer host, from the film digitizer host to the image server over Ethernet, and from the image server to the review stations over fiber. Within the image review station, faults could also occur affecting only imagery. Image storage errors may occur on the disks in the film digitizer host and the image server.

One way to test for these kinds of errors is to store multiple copies of the same test image file at each point in the system and then move copies from point to point. At each point, a comparison is made between the image transferred and the one stored. The use of an image is not strictly required, but it may be convenient from a standpoint of software overhead. What is important is that the volume of data be similar to or greater than that of any image file and that the data set transferred exercise in a predictable fashion all bits and all possible binary values typical of image files.

The requirement for moving image-sized volumes of data stems from a desire to test for random or pseudo-random faults in the communication or storage paths. By increasing the time over which a transfer or storage operation takes place, the higher the probability that random error faults will be discovered.

Figure 21:
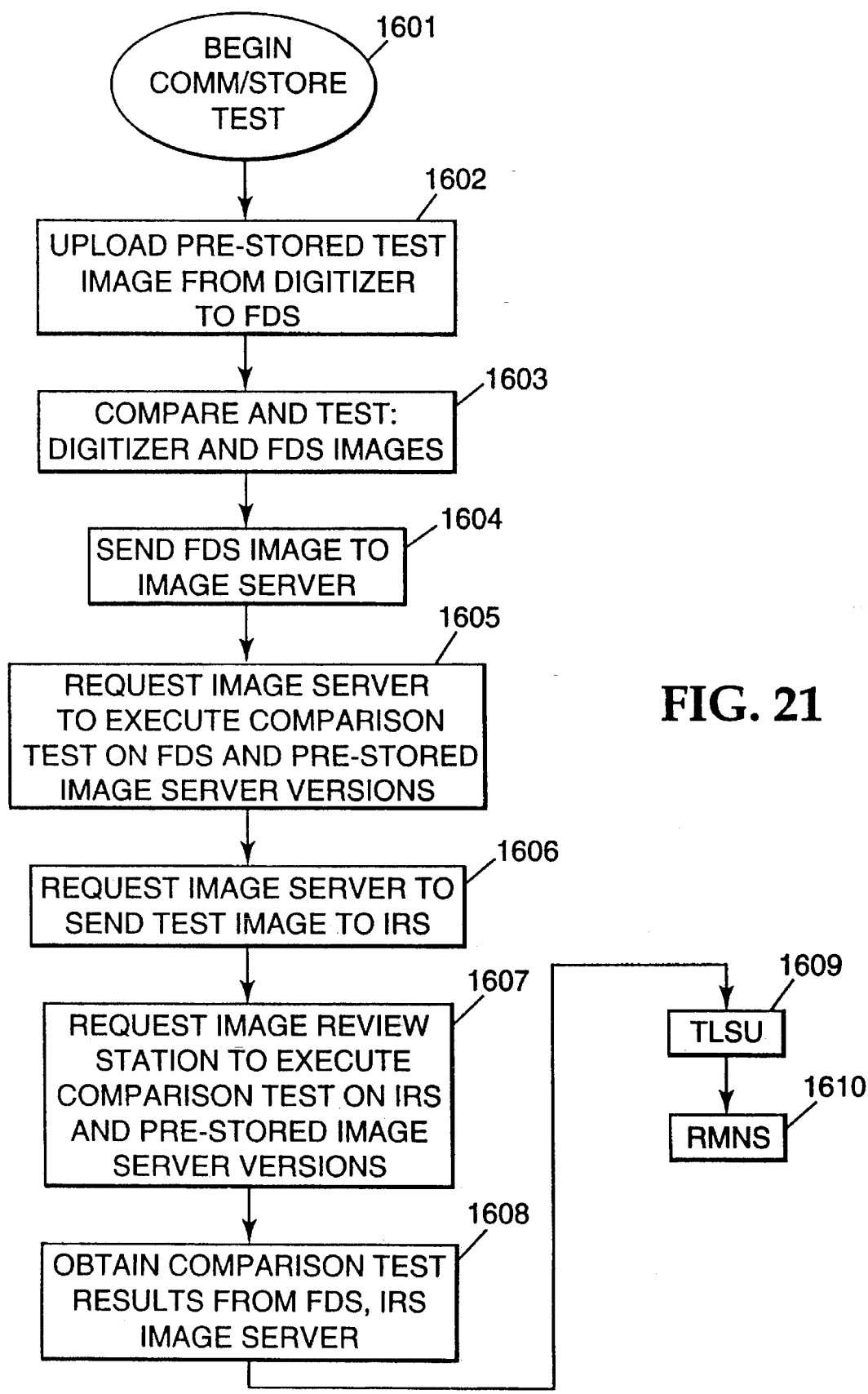
FIG. 21 is a flow chart for the image storage and communications test procedure of FIG. 13.

FIG. 21 shows a process for performing the kind of test described above. The process would propagate copies of stored images up the chain from the film digitizer to the point of display. At each node, an image comparison would be performed and errors recorded. All errors would be harvested into the system where they would be entered into the results log file. This form of testing will provide an added confidence check for all users of the system that image quality control has been addressed at all levels. It is not meant to supersede additional diagnostics to test the buses, CPUs and memories within the host computers used throughout the system.

Automated Image Quality Control Finish Procedure

Upon completion of all the procedures called for and described in FIG. 13, or upon an abort operation from within any of the procedures described above, the finish procedure is invoked. In this procedure, a summary screen is presented to the user which shows the completion status of all other procedures. This screen would be a simple format showing the final status of all of the aforementioned procedures.

Image Review Station Process States

Figure 22:
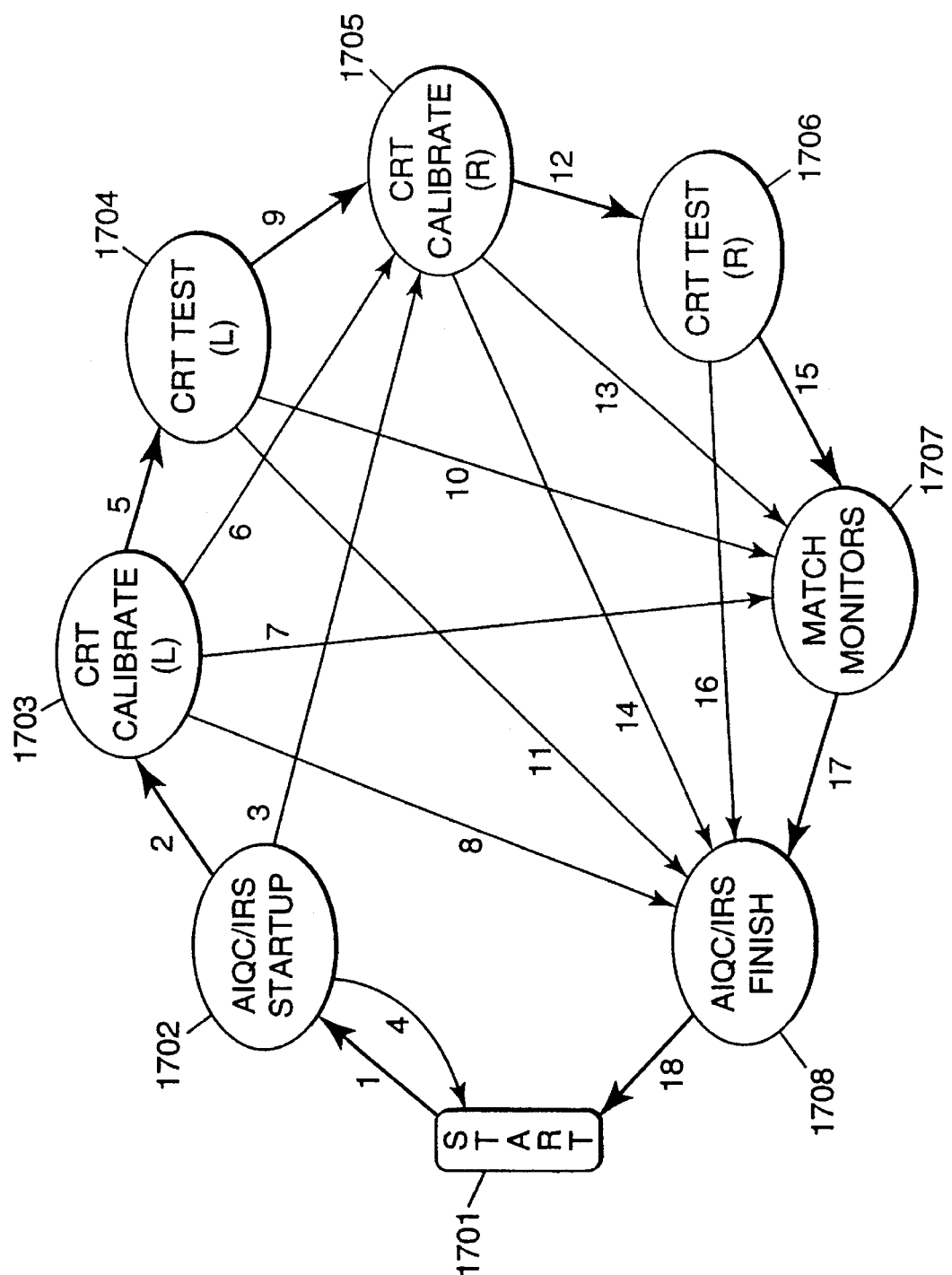
FIG. 22 is a state diagram of the procedures of the automated image quality control process for the image review station of the preferred embodiment of the present invention.

FIG. 22 is a state diagram showing the automated image quality control system applied to the image review stations. As described above, the system is only attempting to provide control of the luminance characteristics of displayed images. This is done to ensure image quality in two main areas.

In the first area, the system will adjust the transfer function from acquired pixel values to displayed luminance such that the soft copy image seen by the users is "matched" to what would be seen by that same user viewing an original film on a light box. Of course, the absolute luminance from the CRT displays will only be a fraction of that from a light box, but the aim here is to preserve the relative contrast in the viewed image. This concept of soft copy to source matching can be extended to other modalities of the preferred embodiment of the present invention including images from a computer radiography unit, MRI or CT scan. In these cases, the objective will be to either match the image originally presented to the operators of these systems once they have window/leveled images, or to the hard copy generated during the normal use of such systems. In the preferred embodiment of the present invention, only the matching of CRT to original x-ray images is described.

In the second main area, luminance characteristics between all of the monitors used in the electronic imaging system will be matched. This feature is especially critical where users have dual headed displays. It is essential that paired images be shown to the user with identical contrast and brightness for comparison. This process will also remove the variation in gamma characteristics between monitors in a pair, and optionally, between all monitors in a given installation.

To perform these two kinds of matching, a series of procedures are executed as shown in FIG. 22. There are three main functional procedures, including CRT calibration 1703, CRT test 1704, and monitor matching 1707. The CRT calibration procedure acquires the characteristics of a given monitor and uses this data in conjunction with predetermined source-to-viewed image transformation function to generate a new display LUT.

Once the new display LUT is generated, it can be downloaded and tested against a series of known images to verify the hardware functionality. In both of these procedures, the luminance data is obtained by augmenting the system on a temporary basis with a photometer having serial digital data output. One such unit, from Tektronics, Model J17, has an RS232 port which can be used with a host computer to command readings and upload luminance readings to the host. In the preferred embodiment of the present invention, a field engineer would connect the photometer to the image review station serving the monitor to be tested. These two procedures prompt the user as to where to place the photometer read head, and thereafter, all data is taken without user intervention.

FIG. 22 shows the sequencing of these calibration and test procedures for both one- and two-headed versions of the image review station. The system provides the option to skip the test and verification of the display LUT hardware.

Once the calibration phase is completed, the monitor matching procedure 1707 is started. In this procedure, the system would attempt to rescale the display LUTs just generated for one or both of the current image review station monitors either to match each other or to all of the rest of the monitors in the system. The exact approach is dictated by additional control variables which specify whether to match at all, and another which says, "match only pairs." In this way, the user has complete flexibility as to how the system monitors will be matched. Note that if the system is matching all monitors, this procedure will act globally upon the display LUTs of all monitors to rescale them to match the upper/lower luminance characteristics just determined. This is a highly recursive process.

CRT Calibration Procedure

Figure 23:
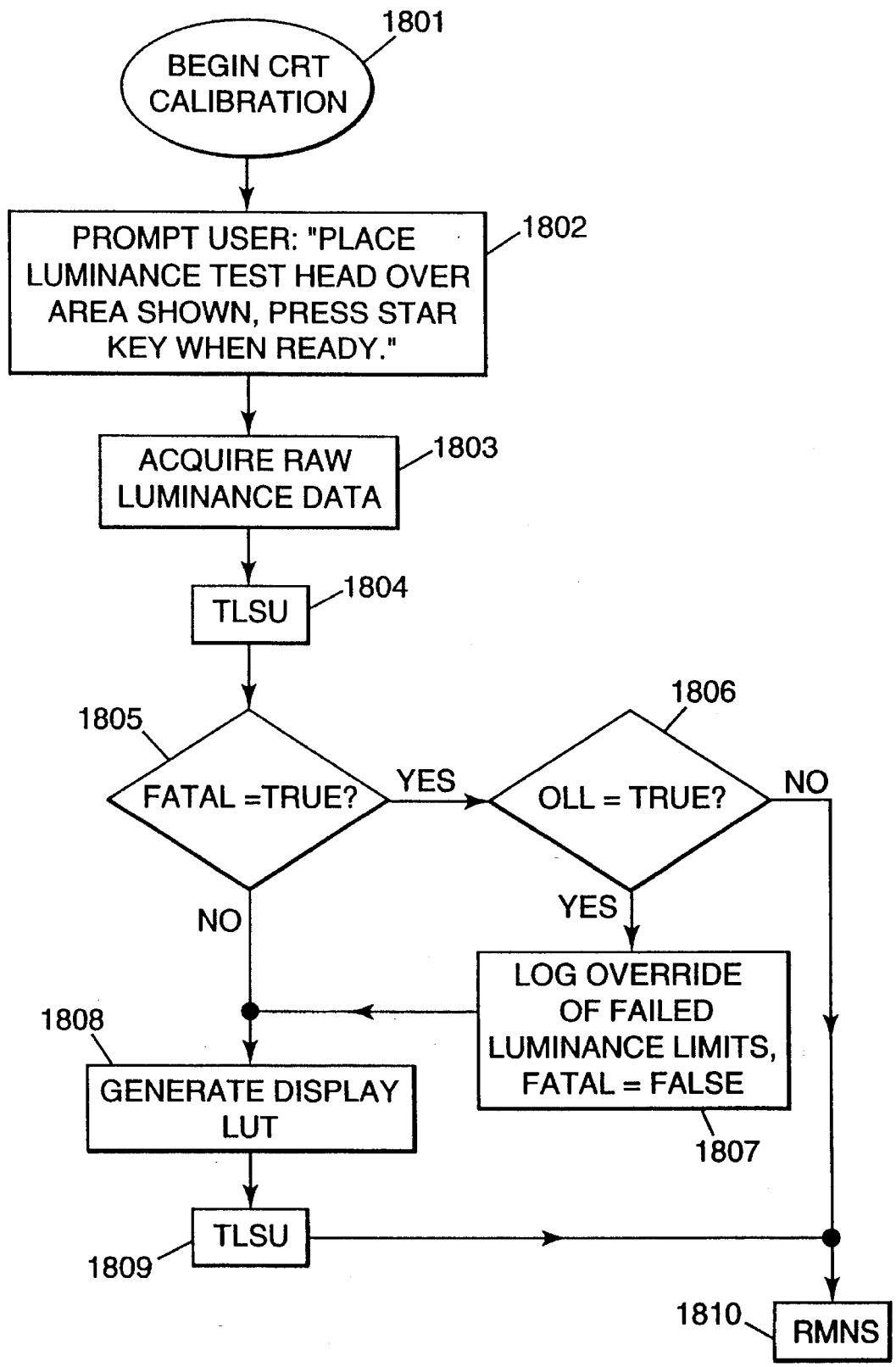
FIG. 23 is a flow chart for the CRT calibration procedure of FIG. 22.

FIG. 23 is a flowchart showing the CRT calibration procedure. The serviceperson would be prompted with an onscreen dialogue and graphics showing where to place to the photometer read head on the monitor to be tested at 1802. Once the placement is confirmed, the raw CRT luminance data would be acquired at 1803. This process performs a series of full screen fills of known digital value followed by a sampling of the luminance reading from the photometer. This produces an array of commanded value to actual luminance that is a characteristic of this monitor's gamma, phosphor, and min/max luminance settings.

After luminance data is harvested, a check would be made against preset minimum and maximum levels to determine if any further manual adjustment of black level and full scale luminance is required. If none are, then a new display LUT is computed. The LUT generation process returns a single metric, the minimum detected slope of the new LUT. This is a measure of the "goodness" of the new display LUT, and if found acceptable, the LUT data is made available for subsequent testing and/or matching with other monitors. The system also allows a forced override of the currently established limits on luminance. This feature allows for calibration of a marginal monitor in the event that it cannot be adjusted due to a weak power supply or an aged CRT.

CRT Test Procedure

Figure 24:
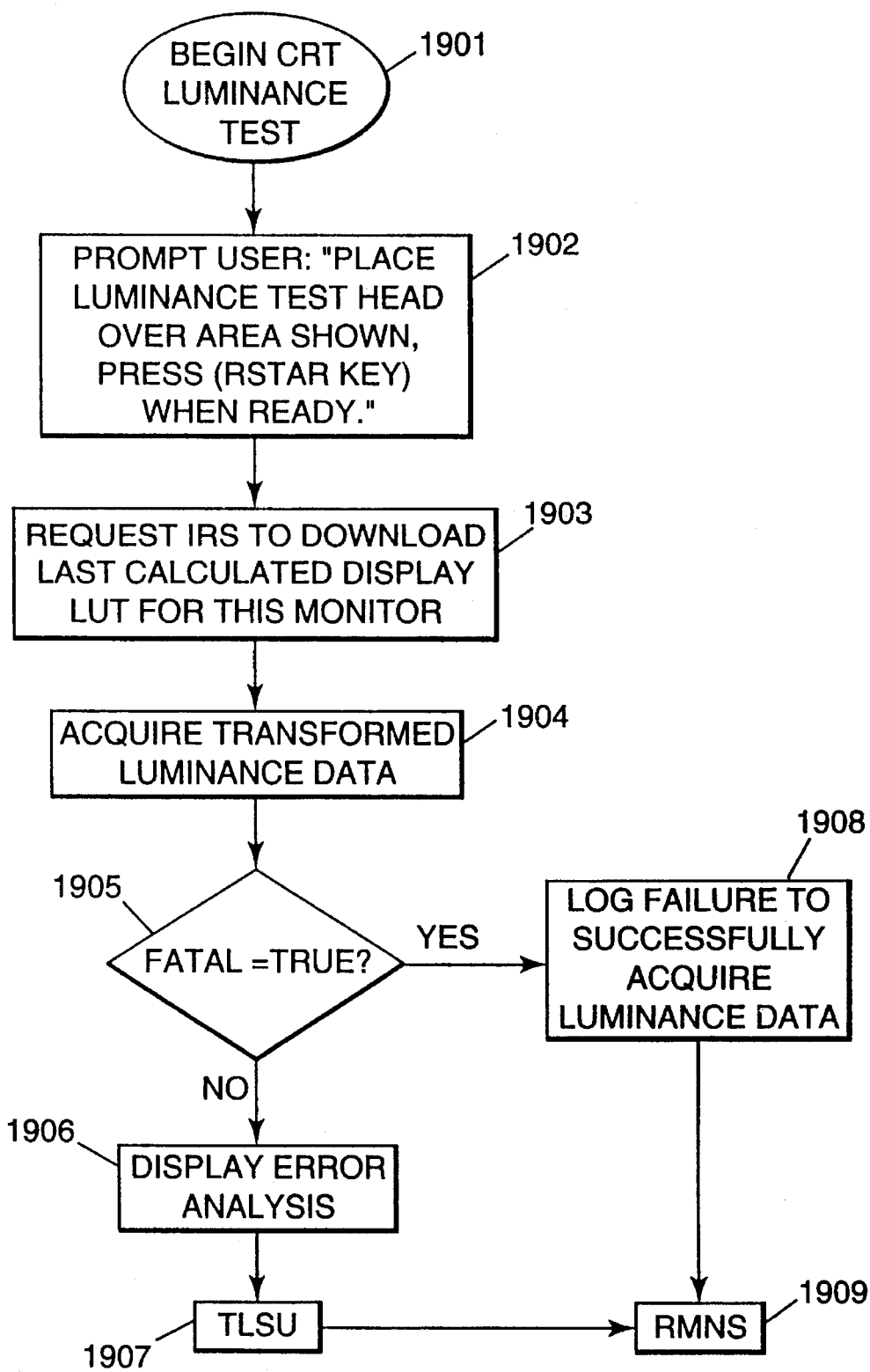
FIG. 24 is a flow chart for the CRT test procedure of FIG. 22.

FIG. 24 describes the CRT test procedure flow. Following the display LUT generation is the verification step where luminance error statistics are found and tested as in other performance metrics. The user is prompted again to ensure that the photometer is correctly placed on the CRT under test at 1902. After confirmation, the display LUT hardware is loaded with the LUT data just calculated at 1903. Next, an acquisition process is started which feeds images of known value to the selected monitor. This procedure is exercising the LUT hardware to obtain the transformed luminance values. Since testing of the LUT hardware may be performed using other, less time-consuming diagnostics, an option is provided to bypass this form of display LUT verification.

Monitor Matching Procedure

Figure 25:
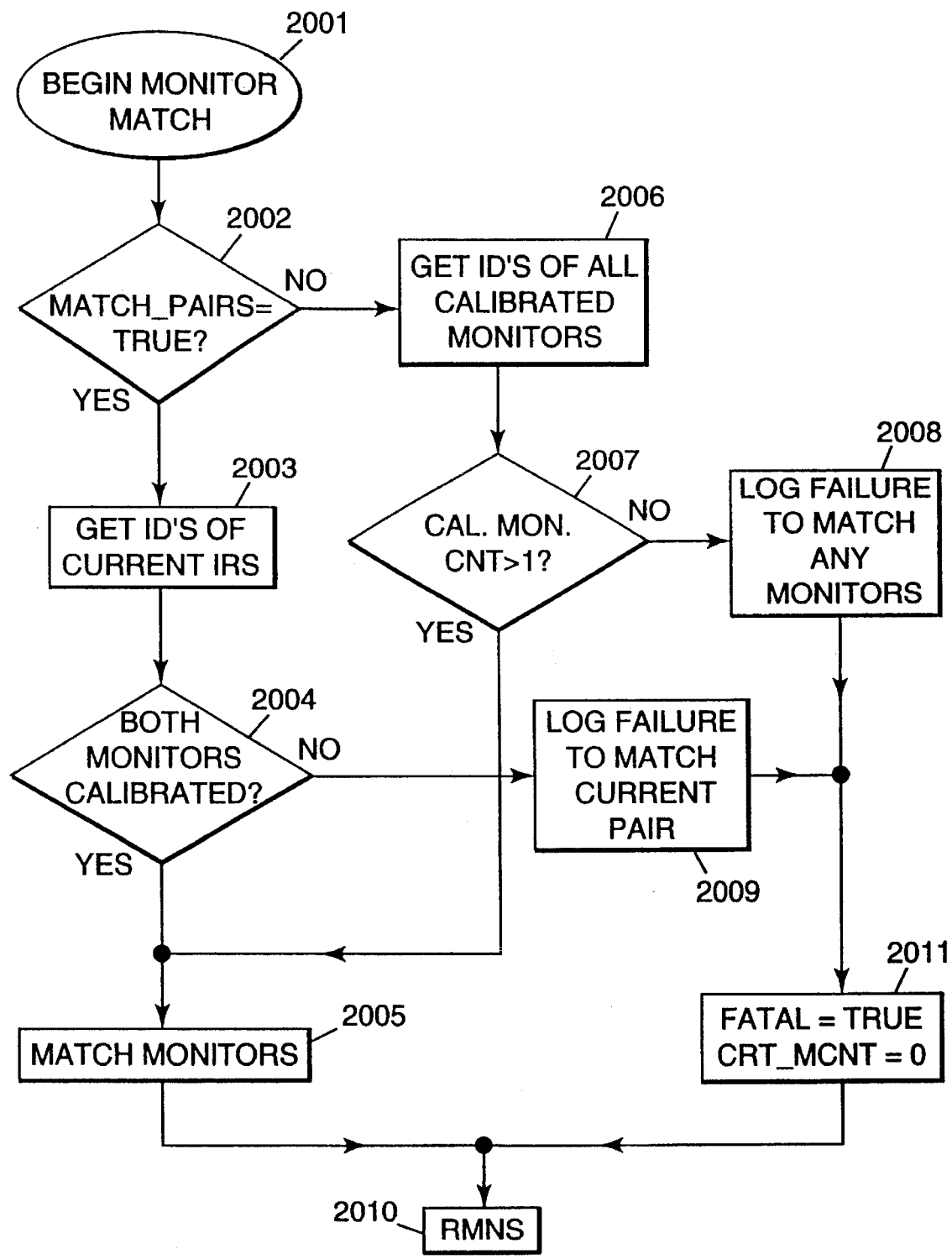
FIG. 25 is a flow chart for the CRT monitor matching procedure of FIG. 22.

FIG. 25 is a flowchart showing the monitor matching procedure. This procedure is only invoked if the user desires to globally match all CRTs. Once this procedure is started, a check is made to see if only matching of monitor pairs is desired. The first step is to verify that there are at least two monitors to match. This is done either by looking at the status of the calibrations just executed, or by inspection of the status from all other monitors in the system. Once the verification is done, the match monitors process is started at 2005. In this process, the monitor with the lowest maximum luminance is found. Then the display LUTs of all monitors with higher luminance are rescaled so that their maximum luminance will match the previously determined minimum upper limit. During this process, access is required to the previously obtained raw characteristic data for a given CRT obtained at some earlier time. The matching process itself does not generate any errors. Rather, it returns a count of the number of rescaled display LUTs along with a set of CRT identification numbers indicating which were rescaled and which were used as the master. The total monitor match procedure only generates a fatal level error when it cannot find at least two monitors upon which to act.

Image Review Station Finish Procedure

As described above in conjunction with the automated image quality control FDS application, all other procedures will pass to the finish procedure 1708 for the image review station process of FIG. 22. The only action at this point in the process is to confirm the screen and exit the test routine. At this time, message are passed and displayed as to the status of this image review station and any other affected image review stations. The summary screen of the finished routine would simply display the final status of the procedures shown in FIG. 13 as either being successful, failed, not operational, aborted or not executed.

CONCLUSION

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

I claim:

1. A method of automatically measuring the performance of a plurality of functional components of an electronic digital imaging system, comprising the steps of:

storing metric thresholds for known good functional components including an image input device and image output device and an image storage memory;

acquiring a sample image from a plurality of reference objects to produce a set of pixel data representative of the plurality of reference objects;

measuring selected attributes from the set of pixel data for image acquisition, image storage and image output functional components and producing therefrom a set of feature statistics;

comparing the set of feature statistics against the metric thresholds; and indicating it any one of the set of feature statistics fall below any one of the metric thresholds and indicating the failure of the functional component which resulted in the any one of the set of feature statistics to fall below any one of the metric thresholds.

2. The method according to claim 1 further including the step of locating a specific failure of a specific functional component which will cause any one of the set of feature statistics to fall below the metric thresholds.

3. The method according to claim 2 further including the step of indicating the cause of failure of the specific functional component which caused a particular one of the set of feature statistics to fall below a corresponding particular one of the metric thresholds.

4. The method according to claim 1 further including the steps of storing a data set of reference features corresponding to the set of feature statistics; and producing the reference object from the data set of reference features for use in measuring the output modality of the electronic digital imaging system.

5. The method according to claim 1 further including the step of calibrating the functional components of the electronic digital imaging system by adjusting values in look up tables each corresponding to each of the system components.

6. The method according to claim 1 further including the step of acquiring the sample image from a reference film as the reference object.

7. The method according to claim 1 further including the step of acquiring the sample image from a three dimensional phantom as the reference object.

8. A method of measuring the geometric distortion in test images processed by the plurality of functional components of an electronic digital imaging system, comprising the steps of:

providing a two-dimensional reference object;

acquiring a sample image from the reference object to produce a set of pixel data representative of the reference object;

locating a registration indicator in the set of pixel data representative of the reference object;

locating a specific region of interest in the set of pixel data representative of the reference object based on the location of the registration indicator;

processing a subset of the set of pixel data within the specific region of interest;

measuring a selected feature within the subset of the set of pixel data within the specific region of interest to produce a measured value;

comparing the measured value against an expected performance value; and indicating if the measured value falls below the expected performance value to indicate a failure in one of the plurality of functional components.

9. The method according to claim 8 further including the step of producing the reference object from a stored data set of reference features to measure the output functional component of the electronic digital imaging system.

10. The method according to claim 8 further comprises measuring the linearity of a line in the reference object, including the substeps of:

performing a region-of-interest calculation on the pixel data within the subset of pixel data to produce a one-pixel width line;

calculating a best fit line to the one-pixel width line; and measuring the maximum deviation of the one-pixel width line from the best fit line as a measurement of the linear geometric performance of the functional components of the electronic digital imaging system.

11. The method according to claim 8 further including the step of acquiring the sample image from a reference film as the reference object.

12. The method according to claim 8 further including the step of acquiring the sample image from a three dimensional phantom as the reference object.

13. A method of measuring the pixel value integrity in images processed by the functional components of an electronic digital imaging system, comprising the steps of:

providing a reference object;

acquiring a sample image from the reference object to produce a set of pixel data representative of the reference object;

locating a specific region of interest in the set of pixel data representative of the reference object;

processing a subset of the set of pixel data within the specific region of interest;

measuring a selected feature within the subset of the set of pixel data within the specific region of interest to produce a measured value;

comparing the measured value against an expected performance value; and indicating if the measured value fall below the expected performance value; and identifying streaks in the reference object, comprising the substep of performing a two-pass, two dimensional background estimate on the pixel data.

14. An automated image quality control system, comprising:

a plurality of input modalities;

a plurality of output modalities;

an image storage memory;

a processor connected to the image storage memory, the plurality of input modalities and the plurality of output modalities and having means for executing the following computer-executed program steps:

storing metric thresholds for known good system components included in all modalities;

acquiring a sample image from a reference object to produce a set of pixel data representative of a physical reference object;

measuring selected attributes from the set of pixel data and producing therefrom a set of feature statistics;

comparing the set of feature statistics against the metric thresholds;

indicating if any one of the set of feature statistics fall below any one of the metric thresholds and indicating the failure of a specific system component which resulted in the any one of the set of feature statistics to fall below any one of the metric thresholds.

15. The automated image quality control system of claim 14 further comprising:

a first look up table connected to the plurality of input modalities;

a second look up table connected to the plurality of output modalities;

the processor connected to the first look up table and the second look up table and further having means for executing the following steps:

storing first adjustment values in the first look up table in response to calibration of the plurality of input modalities; and storing second adjustment values in the second look up table in response to calibration of the plurality of output modalities.

16. The automated image quality control system of claim 15 wherein the processor is further operable for calculating the first adjustment values and the second adjustment values.

17. An automated image quality control system, comprising:

storage means for storing metric thresholds for a plurality of known good system components;

acquisition means for acquiring a sample image from a reference object having a plurality of reference features to produce a set of pixel data representative of the reference features of the reference object;

measurement means for measuring selected attributes from the set of pixel data and producing therefrom a set of feature statistics;

comparison means for comparing the set of feature statistics against the metric thresholds; and indicator means for automatical indicating a failure if any one of the set of feature statistics fall below any one of the metric thresholds and for indicating a one of the plurality of system components which caused the failure.

18. A method of measuring the geometric distortion in images processed by the functional components of an electronic digital imaging system, comprising the steps of:

producing a reference object from a stored data set of reference features to measure the output functional component of the electronic digital imaging system.;

acquiring a sample image from the reference object to produce a set of pixel data representative of the reference object;

locating a registration indicator in the set of pixel data representative of the reference object;

locating a specific region of interest in the set of pixel data representative of the reference object based on the location of the registration indicator;

processing a subset of the set of pixel data within the specific region of interest;

performing a region-of-interest calculation on the pixel data within the subset of pixel data to produce a one-pixel width line;

calculating a best fit line to the one-pixel width line;

measuring the maximum deviation of the one-pixel width line from the best fit line as a measurement of the linear geometric performance of the functional components of the electronic digital imaging system to produce a measured value;

comparing the measured value against an expected performance value; and indicating if the measured value falls below the expected value.

19. A method of measuring the pixel value integrity in images processed by the functional components of an electronic digital imaging system, comprising the steps of:

providing a reference object;

acquiring a sample image from the reference object to produce a set of pixel data representative of the reference object;

locating a specific region of interest in the set of pixel data representative of the reference object;

processing a subset of the set of pixel data within the specific region of interest;

measuring a selected feature within the subset of the set of pixel data within the specific region of interest by performing a two-pass, two dimensional background estimate on the pixel data to identify streaks in the reference object and producing thereby a measured value;

comparing the measured value against an expected performance value; and indicating if measured value falls below the expected performance value.

* * * * *